US011645932B2

(12) United States Patent
Bertolli et al.

(10) Patent No.: US 11,645,932 B2
(45) Date of Patent: May 9, 2023

(54) MACHINE LEARNING-AIDED MIXED REALITY TRAINING EXPERIENCE IDENTIFICATION, PREDICTION, GENERATION, AND OPTIMIZATION SYSTEM

(71) Applicant: Avrio Analytics LLC, Knoxville, TN (US)

(72) Inventors: Michael Bertolli, Knoxville, TN (US); Alicia Caputo, Knoxville, TN (US); Jason Therrien, Houston, TX (US)

(73) Assignee: Avrio Analytics LLC, Knoxville, TN (US)

( * ) Notice: Subject to any disclaimer, the term of this patent is extended or adjusted under 35 U.S.C. 154(b) by 0 days.

(21) Appl. No.: 17/715,557

(22) Filed: Apr. 7, 2022

(65) Prior Publication Data

US 2022/0327945 A1 Oct. 13, 2022

Related U.S. Application Data

(60) Provisional application No. 63/171,713, filed on Apr. 7, 2021, provisional application No. 63/297,520, filed on Jan. 7, 2022.

(51) Int. Cl.
*G09B 5/02* (2006.01)
(52) U.S. Cl.
CPC ....................................... *G09B 5/02* (2013.01)
(58) Field of Classification Search
None
See application file for complete search history.

(56) References Cited

U.S. PATENT DOCUMENTS

| 7,552,480 B1 | 6/2009 | Voss |
| 2004/0119662 A1 | 6/2004 | Dempski |
| 2016/0077547 A1 | 3/2016 | Aimone et al. |
| (Continued) | | |

OTHER PUBLICATIONS

Huynen, Jean-Louis, et al., Towards design recommendations for training of security critical agents in mixed reality environments. Proceedings of the 32nd International BCS Human Compute Interaction Conference 32, 2018, Retrieved on Jul. 10, 2022 from.
(Continued)

*Primary Examiner* — James B Hull
(74) *Attorney, Agent, or Firm* — Chambliss, Bahner & Stophel, P.C.; Stephen D. Adams

(57) ABSTRACT

A mixed reality (MR) training system includes an identification algorithm (ML1) that identifies incidents of concern (IOCs) based on an incident report data set and related contextual data. Each IOC occurs in the data set with a frequency at least equal to a pre-determined threshold or the resulting consequence is at least equal to a different pre-determined threshold. The system also includes a prediction algorithm (ML2) configured to identify predicted changes in the frequency or contextual data of incidents, an experience generation algorithm (ML3) configured to generate an MR training experience based on IOCs identified by ML1 and the predictions of ML2. A fourth algorithm (ML4) tailors and optimizes MR generated training experiences based, in part, on (i) changes in the incident report data or contextual data or (ii) performance data or biometric response data received during or after a user's interaction with the MR training experience.

14 Claims, 13 Drawing Sheets

(56) References Cited

U.S. PATENT DOCUMENTS

2016/0239080 A1    8/2016    Marcolina et al.

OTHER PUBLICATIONS

International Search Report for US/PCT2022/023835, dated Jul. 29, 2022, 9 pages.
Livington, Mark A., et al., Military applications of augmented reality, Handbook of augmented reality, 2011, pp. 671-706.
Perfecto, Cristina, et al., Taming the latency in multi-user VR 360; A QoE-aware deep learning-aided multicast framework, IEEE transactions on communications 68.4, 2020, pp. 2491-2508.

MACHINE LEARNING-AIDED MIXED REALITY TRAINING EXPERIENCE IDENTIFICATION, PREDICTION, GENERATION, AND OPTIMIZATION SYSTEM

CROSS-REFERENCE TO RELATED APPLICATION

This application claims the benefit of U.S. Provisional Application No. 63/171,713, filed Apr. 7, 2021, and entitled REAL-TIME TRACKING OF ARBITRARY OBJECTS IN MIXED, VIRTUAL AND AUGMENTED REALITY DEVICES and also the benefit of U.S. Provisional Application No. 63/297,520, filed Jan. 7, 2022, and entitled AI-GENERATED CONTENT TRAINING CONTENT; each of the foregoing applications is incorporated herein by reference in its entirety.

FIELD

This invention relates generally to systems and methods for identifying, generating, and optimizing training exercises, including through the use of real-time geometric mapping and occlusion methods and also the real-time tracking of arbitrary objects in virtual reality ("VR") environments, augmented reality ("AR") environments, and mixed VR and AR ("MR") environments.

BACKGROUND

In many industries, participation in training exercises is important for developing and maintaining expertise in skills needed for carrying out the various tasks associated with the occupations in those industries. Simulated training environments and exercises are particularly beneficial for those engaged in inherently hazardous and risky occupations, such as first responders (e.g., fire and police) and military personnel, where the training relates to high-risk/low-occurrence and high-risk/high-consequence events. Outside of the training context, simulated experiences are also frequently used in other various industries, including the entertainment industry (e.g., video games).

There is a need to improve the realism, speed, relevancy, timeliness, quality and coverage of virtual training experiences for critical, dynamic scenarios, especially for novel situations and situations involving high-risk/low-occurrence events.

NOTES ON CONSTRUCTION

The use of the terms "a", "an", "the" and similar terms in the context of describing embodiments of the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic.

The use of any and all examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

A virtual reality ("VR") environment is one that provides total immersion of the user without introducing elements of the user's actual environment. Any interactions occur entirely within the virtual environment and not within the physical world. Typically, a VR environment is created using computer-generated or real images. Peripherals, such as gloves, goggles, controllers, etc. (i.e., "peripherals"), detect the user's movements, typically including movement of the user's head and hands, translate that movement into the virtual environment to allow the user to interact with the VR environment. On the other hand, an AR environment is one where data (e.g., computer-generated experiences, information, etc.) are overlaid onto the physical world, but where all interactions occur within the physical world. Typically, AR environments use a display screen, glasses, goggles, etc. to present the data. Finally, a mixed reality ("MR") environment is essentially a combination of VR and AR environments, where virtual objects are integrated and interact with the physical world in real time. Like VR, MR peripherals may also be used in connection with MR environments, which devices are typically specifically manufactured for direct connectivity and interaction with the environment created. In the description that follows, the term "MR" or the phrase "mixed reality" may be used to refer to any of AR, VR, or MR unless otherwise specifically noted.

The term "MR system" refers to the computer, machine, etc. that generates the virtual content or experience for an MR environment. Additionally, the term "peripheral" or "MR peripheral" is used to refer to the tools (e.g., gloves, goggles, helmets, etc.) that a user might employ to view and interact with that MR environment.

The term "incident report" includes, but is not limited to, governmental or pseudo-governmental agency reporting, open source/public first responder datasets, first responder dispatch and radio sources, video capture sources (e.g., body cams, dashcams), emergency response communication data feeds (e.g., FirstNet® network) and news and social media sources (e.g., Twitter® feeds). Preferably, such data includes detailed information, where available, on those persons involved in each incident (including descriptive information, such as age), situational information (e.g., type and number of vehicles in a vehicular accident), response information (including details of responders, procedures, and performance) and general outcome. The term "incident report data" refers to this general body of information that may be received from any of the information sources discussed above as well as other similar sources. The term "contextual data" includes, but is not limited to, market data, population data (e.g., census data, consumer buyer data, vehicle traffic, health), environmental data (e.g., weather, season), geographic/geospatial data (e.g., incident location, topography), and policy and law data. This contextual data may be important or helpful in appreciating or more fully understanding the incident report data but may not necessarily be directly related to the incident report data. The term "predicted data" refers to a set of data that is predicted to occur by the present system but that might not have actually occurred in the incident report data or the contextual data. For example, the system might predict demographic changes to an area that are meaningful (e.g., more purchases of electric vehicles (EV) that could alter the consequence of EV battery fire incidents).

SUMMARY

The above and other problems are addressed by a mixed reality (MR) training system that includes a scenario identification algorithm (ML1) configured to take, as inputs from monitored data sources, incident report data related to one or more incidents and contextual data that relate to the one or more incidents, and to identify incidents of concern (IOCs). Each IOC is an incident that appears in the data set and that occurs in the data set with a frequency at least equal to a pre-determined frequency threshold or wherein contextual data related to the IOC indicates a resulting consequence that is at least equal to a pre-determined resulting consequence threshold.

In certain embodiments of the invention, the system further includes an experience generation algorithm (ML3) configured to generate an MR training experiences based on a data set that may include incident report data related to one or more incidents, including one or more of the IOCs identified by ML1, contextual data that relates to those incidents, or a library of experience building blocks. Those building blocks might include, for example, human entities, environment, experiential MR content, or other MR content that is created for use or is otherwise useful in the generation of MR experiences.

In certain embodiments of the present invention, the system further includes a scenario prediction algorithm (ML2) that is configured to, based on the incident report data and contextual data, identify predicted data that includes either (i) predicted changes in the frequency of an identified type of incident occurring in the incident report data, (ii) predicted changes in the consequences of an incident, or (iii) predicted changes in the contextual data of the identified type of incident. Preferably, ML3 is configured to generate MR training experiences based on at least one of the IOCs identified by ML1 or the predictions of ML2. In certain embodiments, the system also includes a training experience tailoring and optimization algorithm (ML4) that is configured to tailor and optimize MR training experiences previously generated by ML3. The tailoring and optimization carried out by ML3 is preferably based on user performance data, biometric response data, and/or user demographic data.

BRIEF DESCRIPTION OF THE DRAWINGS

Further advantages of the invention are apparent by reference to the detailed description when considered in conjunction with the figures, which are not to scale so as to more clearly show the details, wherein like reference numerals represent like elements throughout the several views, and wherein.

DETAILED DESCRIPTION

Figure 1:
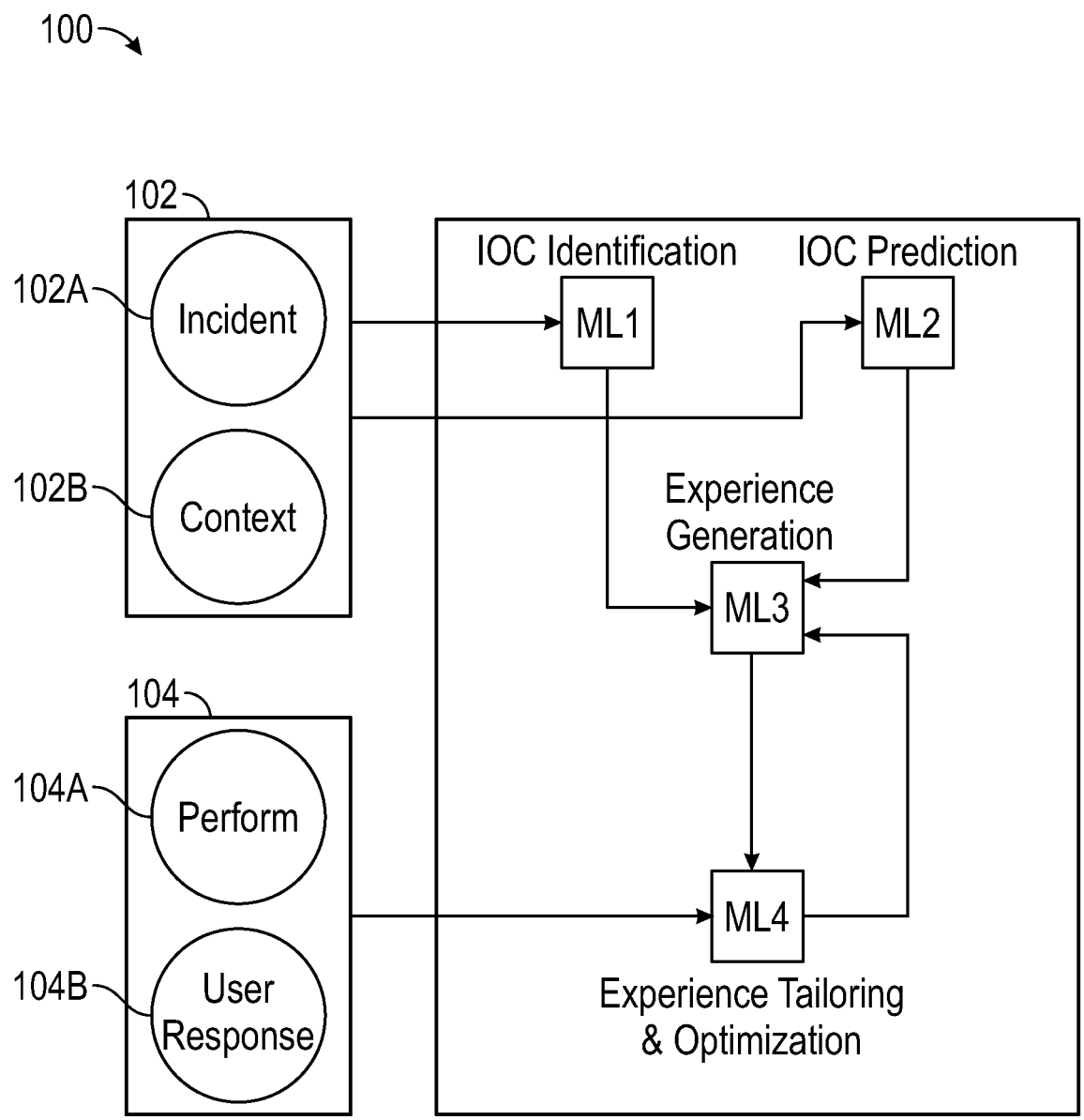
FIG. 1 depicts a portion of a mixed reality (MR) training system according to an embodiment of the present invention.

Virtual reality, augmented reality, and mixed reality training systems are helpful in providing realistic training experiences. However, there are a number of problematic issues associated with current training systems and there are a number of ways that these systems could be improved to provide even more effective training systems, which the currently-disclosed system provides, as further detailed below.

Section 1: Experience Generation & Customization

When simulated training experiences are used for training programs and also in other applications, one important factor for its success and effectiveness is that the experience should be sufficiently realistic, relevant, and should place the participant in a physical state that is similar to the physical state that they would be in during a real-life event. In this regard, developing relevant and realistic experiences is central to providing a successful training program. However, for police, emergency medical services (EMS), and other training areas where dynamic, complex environments are necessary, there is a natural limitation in providing timely training of new scenarios and experience development can be a severe bottleneck in providing a successful training program. This is especially true in cases where the experience uses or requires human role players. Two specific examples of such areas are given below.

EMS frequently train on patient intake, triage, and treatment for high-risk, high-stress scenarios (e.g., multi-casualty car accidents, natural disasters). Their training commonly entails the use of human role players in order to capture the critical nuances of patient interactions and medical assessments that are not readily represented in most current training simulators. In particular, patient interactions are highly dynamic—and in that respect even human role players often only provide training coverage for a small subset of all possible scenarios that is driven by individual or organizational experience (e.g., severe mental health issues in a patient may only be exhibited if a role player has prior experience with such a scenario). As an example, the anthrax attacks that took place in the early 2000s introduced an unprecedented dynamic for EMS in which the potential for novel biohazard exposure became very plausible. The same may possibly be said about EMS response dynamics due to the more-recent COVID-19 pandemic. However, the coordination and design of timely, relevant experiences for these kinds of events is highly dependent on logistically-challenging factors (e.g., the availability of role players) as well as limitations in experience design (e.g., instructor chooses patient conditions from their own expertise or limited sets of training libraries).

Next, police train (in some cases, by mandate) on proper response and de-escalation techniques. This training is focused on the officers' interactions with individuals in various circumstances, ranging from domestic violence to mental health crises. It is common for actors/role players to take the role of the victim and/or subject, where these role players can be other officers. Simulators are common, particularly for use-of-force or shoot/no-shoot training. But, even here, the simulations most commonly feature video recordings of actors enacting the various parts. Simulations can be dynamic to a limited extent through "branching," where the instructor can choose which video clip to play next, altering the disposition and actions of the role players. While firearms and non-lethal tools are often present and used in these training scenarios, the focus is not on firearms training (e.g., accuracy, technique). While such training often has low logistical hurdles because of the availability of simulation, it is hampered by the limitations of user-chosen branching dynamics and the use of role players (e.g., all possible branches must be recorded, and an instructor cannot manage branching options of more than a dozen).

For example, the anthrax attacks that took place in the early 2000s introduced an unprecedented dynamic for EMS in which the potential for novel biohazard exposure became very plausible. However, training experiences for medical response under such new hazards was not readily available due to the novelty of the situation. The same may possibly be said about EMS response dynamics due to the more-recent COVID-19 pandemic. While training developers rapidly move to address these gaps in curriculum, the development of relevant training experiences may still require months or even years after the onset of these incidents, which is not timely.

The same can be seen in policing. For example, the political protests and passive-aggressive non-compliance of 2020 became a novel threat to public and officer safety, but little to no training experiences were available for officers until far after those events. In another example, in December 2021, Denver Metro area police departments were faced with an active shooter that targeted specific victims over a large geographic area. This presented a novel scenario for which the departments were not adequately prepared. Again, little to no training experiences or training systems for this type of multi-departmental engagement were, at the time or even now, available to heighten the expertise and performance of the police.

In many of these cases, the lack of relevant training is largely due to the fact that training experiences are derived from real-world scenarios and experiences, either of the individuals or from the collective experiences of institutions and fields of expertise. Additionally, training experiences, especially training experiences that are focused on dynamic scenarios that require human role players (either in person or captured in simulation), takes significant time to develop.

Now, with reference now to FIG. 1, there is shown a mixed reality (MR) training system 100 according to an embodiment of the present invention. This system 100 is designed to identify and predict incidents of concern (IOCs), which are incidents or scenarios where the users of the system might want or need training and the system's identification of these IOCs is essentially a recommendation from the system to the user as to the types of scenarios that the user might benefit from. Preferably, the system is configured to identify IOCs that are novel and/or that have a high associated cost/consequence and to provide or recommend for improving user's proficiency for the incidents identified. The system may also be used to identify and recommend training for incidents that are not novel and that do not necessarily have a high consequence but where the user groups still require improvement. For example, rescuing cats from trees is generally thought of as a routine task for fire departments with relatively low consequences. However, if a particular fire department has demonstrated a poor ability to rescue cats from trees, the system might identify this as an IOC for that particular organization and suggest training to further develop that skill.

As discussed below, this recommendation may be based on a number of factors, including the occurrence of other similar incidents, the prediction of other similar incidents occurring in the future, the performance of a user (or group/agency as a whole) in past trainings, the biometric response of users, the demographic information of users/groups/agencies using the system, etc. The system 100 is also preferably configured to generate training experiences based on the IOCs identified and predicted to then, over time, customize or optimize those experiences based on information-centric and/or user-centric information that is received by the system.

Preferably, system 100 is provided with one or more machine learning algorithms for identifying and predicting training experiences, generating training experiences for user consumption, and/or tailoring and optimizing training experiences. In the illustrated embodiment, system 100 includes a scenario identification algorithm ML1, a scenario prediction algorithm ML2, an experience generation algorithm ML3, and a training experience tailoring and optimization algorithm ML4. Each of these algorithms (ML1 through ML4) is valuable and useable on its own or two or more of them may be used together as a system, such as in system 100. As further detailed below, system 100 uses algorithms ML1 -ML4, in combination with data acquired from various data sources, to identify, predict, generate, tailor and optimize MR training experiences for users of the system.

A variety of data sources provide both high-level context and detailed information on topics relevant to first responders, such as police and EMS, as well as to others. Within these data sources, indications of current or emerging relevant incidents may become evident. For example, social media trends may indicate a broader movement towards social unrest in urban areas that are relevant to police forces. In other cases, behaviors of large gatherings, (e.g., at concert events), may prompt anticipation of novel group dynamics in large gatherings. Social media and traditional news outlets provide incredible, nearly real-time telemetry into what is happening in our society. These data sources can be further augmented with available open source data, such as that provided by police or fire departments, and non-public data sources, such as intelligence reports and non-public police or EMS reports.

In preferred embodiments, ML1 is configured to take, as inputs from a first data source 102, incident report data 102A related to one or more incidents and contextual data 102B that relate to the one or more incidents. Preferably, first data source 102 is monitored and updated in real time with new incident report and contextual data. From those inputs, ML1 identifies incidents of concern (IOCs) for which training content may be created by the system 100. From those same data, ML1 also preferably also identifies (i) the likelihood of incidents occurring again in the future and (ii) how novel the incidents are compared to other incidents.

In many cases, the identification of IOCs is predicated on observable patterns of behavior available in incident reports, news reports, intelligence reports, briefings, etc. At its most basic level, monitoring data sources, such as first data source 102, especially when monitored and updated in real-time with new incidents and contextual data, can provide timely indicators of scenarios that are likely to playout in the near future. For example, news of protests in West Coast cities can prompt appropriate training for Midwest police departments and EMS in cities with similar population sizes. Additionally, incident report data 102A can be coupled with market-level contextual data 102B to identify what areas are most likely to see similar incidents. This would, for example, allow fire departments to train for a particular event even before they ever saw a similar issue in their own service area and before such incidents become common enough to be addressed by regional or national training organizations.

The approach of recognizing IOCs treats the data as a leading indicator rather than predicting never-before-seen scenarios and the data set is anticipated to be quite large; therefore, it is important in the identification of IOCs to separate signal from noise. Therefore, ML1 is preferably configured to filter and prioritize the data when identifying IOCs and to only identify an incident as an IOC when (i) the incident occurs in the data set with a frequency at least equal to a pre-determined (e.g., tunable) frequency threshold or (ii) wherein contextual data related to the IOC indicates a resulting consequence that is at least equal to a pre-determined (e.g., tunable) resulting consequence threshold. In certain embodiments, the resulting consequence used in this determination is based on contextual data related to various consequence factors, including the loss of life, the economic impact, the value or amount of property destroyed as a result the incidents, social or political costs or results (e.g., election results, voting numbers, etc.). As discussed above, in certain cases, past performance of an individual or group (e.g., a police or fire department) in a particular training scenario, even if that scenario is not novel, may constitute an IOC when the individual or group has shown failure rates in the past (e.g., poor cat rescuing skills).

IOCs can then be compared to incidents for which training experiences are already available and then, when new training experiences are generated and tailored by ML3 and ML4 (as discussed further below) prioritized according to novelty. Additionally, ML1 is preferably configured to identify "enhancing" factors within the contextual data 102B that is common between two or more of the incidents and that impacts the likelihood of that incident occurring again or that impacts how novel the incident of the IOC is compared to other incidents. For example, some incidents may be of low priority to firefighters overall, but high priority to firefighters responding to ski resorts in Colorado during the winter months where the fire department has an average age over 35 years old. In this example, enhancing factors might include the location (i.e., Colorado) and the firefighter's age (i.e., 35 years old).

Each of the other algorithms (i.e., ML2 through ML4) may be configured to use, but is not required to use, information provided by the first data source 102 or (second data source 104, which is further discussed below), including incident report data and contextual data. Each of the algorithms is preferably flexible enough to receive and use any time or amount of data that is made available to it. This flexibility would permit the system 100 to be utilized by different entities that have differing amounts or types of data available to them. For example, the data available to one police department might not be available to another police department due to jurisdictional limitations. Similarly, a first amount of data might be available to the FBI, whereas a greater amount of data might be available to certain areas of the military as a result of clearance issues.

In many cases, the data analysis on existing or past incidents can provide predictive insight into future incidents as well. As such, ML2 is preferably configured to use information obtained from first data source 102 to identify either (i) predicted changes in the frequency or consequence of an identified type of incident or (ii) predicted changes in the contextual data of the identified type of incident. To be clear, ML1 identifies IOCs in the data that is currently available, whereas ML2 predicts IOCs (or changes to IOCs) that might appear in the data in the future based on the data that is currently available. Thus, ML2 can be used to predict incidents that are not, at present, IOCs but that might become IOCs in the future due to a predicted change in their frequency or due to predicted changes in their contextual data or changes in their consequence. As shown in FIG. 1, this predicted data 102C (provided by ML2) may also be a third category of data provided by first data source 102 that may be used in the generation of new training experiences. This would, therefore, allow system 100 to preemptively provide training experiences relevant to these predicted new IOCs.

Preferably, ML2 mathematically identifies possible incidents based on either an extrapolation or combination of incidents within the first data source 102. Various methods for this identification process would include combinatorics, neural networks, statistical inference, and the like. For example, if the data includes a large number of single-family residential fires, ML2 might predict that the contextual data associated with the IOC (i.e., a structural fire) might change from single-family homes to multi-family fires under similar weather conditions or if wind directions changed in certain topologies (despite it not having occurred in the data in the past). ML2 might identify less obvious combinations or changes. For example, a high frequency of car accidents seen in the data may result in a cross-over with another, independently seen incident with high frequency, such as a mental health crisis resulting in a scenario of a car accident with victims undergoing a mental health crisis. In another example, high consequence events involving hazardous chemical releases might be present in the data and they might be correlated by ML2 with other events, such as car accident incidents or active shooter incidents, which could result in the creation of novel training experiences.

Preferably, ML2 functions as a type of "scenario optimization" and preferably includes an objective function that maximizes the likelihood of occurrence and/or novelty and relevance of the incidents predicted. For this purpose, various generative methodologies exist, including evolutionary algorithms, reinforcement learning algorithms and generative-adversarial neural networks. Regardless of the specific implementation, ML2 preferably generates predicted incidents and ensures their plausibility through optimization of the objective function. In certain embodiments, ML2 provides segmented predictions (e.g., predicting by geography) and can be trained incrementally on varying levels of data resolution (e.g., leveraging transfer learning to pre-train on public data and refine predictions specific to an agency or department).

As discussed above, the ML1 and ML2 algorithms provide a means and method for programmatically and predictively producing training scenarios or incidents. However, ML1 and ML2 do not generate the necessary content for each scenario. Instead, they produce what amounts to a contextual prompt or description of a scenario that can be fed into ML3 and ML4. As noted above, system 100 also includes ML3, which may be used to programmatically (i.e., automatically) generate an MR training experience based on at least one of the incidents considered or the IOCs identified by ML1 or the incidents predicted by ML2. It is noted, however, that the contextual prompts from ML1 and ML2 are not necessary for ML3 to generate MR training experiences. Instead, the same type of contextual prompt could be provided by a human or other system and therefore this generation algorithm is independently valuable. In each case, these prompts generally serve to condition the probabilities of statistical generation of MR training experiences by ML3 and have been demonstrated with, for example, GTP-3 (Brown et al, arXiv:2005.14165; text generation) and DCGAN (Radford et al., arXiv:1511.06434; image generation), or Deepfakes (video/human generation). Evolutionary and reinforcement learning algorithms can also be used.

In certain embodiments, ML3 generates MR training experiences incorporating at least one of or is directed exclusively to one of the following pre-generated MR experience content building blocks: human entities, environment, experiential, which are discussed in more detail below. Some or all of this content from any of these building blocks may be created "on the fly" by ML3 or may be obtained from a pre-existing library of content. In any case, an advantage of separating the generation process into multiple parts is that machine learning algorithms, such as ML3, generally perform best when directed towards a specific task.

The Human Entities building block would include human avatars that might be utilized in the MR experience. There are a number of important aspects for each building block that can be modified to vary the realism of the generated MR experience. For example, a first aspect of this building block might include number and relationship of human entities, including whether they are cast as adversaries, victims, or patients. Another aspect is speech. The script used by the human avatars in the training content is often one of the most crucial aspects of an immersive and realistic experience. By taking in scenario prompts, as well as additional prompt data (e.g., actual conversations between police and subjects from body cams), an extremely realistic script can be generated my machine learning.

Another aspect of the Human Entities building block is movement and physical behavior. The physical movement and behavior of the human avatars can be more important than their speech. For example, police often rely more heavily on body language than speech during de-escalation, and EMTs may rely on visual confirmation of breathing (e.g., chest rising and falling). Additionally, the manner in which an individual moves through the scenario can change the situation dramatically (e.g., approaching a police officer, running towards another player and/or avatar). The physical behavior is tightly coupled with the number and relationship of the avatars as well, where coordinated or adversarial behaviors may be relevant (e.g., group of protesters coordinating their movements, or the victim of domestic assault being present during questioning and reacting fearfully). In preferred embodiments, this physical behavior is handled by a combination of animations, physics simulation and object movement in the MR content, or via recording for video content (which can be 2D or 3D, e.g., body tracking).

A final aspect of the Human Entities building block includes visual representation. The visual representation of the human avatars, including their dress and what they are carrying/have with them, can be very important for creating dynamic scenarios. This might range from demographics (e.g., age, gender) to visible injuries (e.g., twisted limb, bloody head, eye discoloration) that provide critical context and situational awareness, as well as detailed information to the responder (e.g., EMT assessments often include contributing factors that may indicate a worse overall condition for a patient). It also introduces methods for placing ambiguity in the scenario (e.g., a subject holding a telephone that may also look like a weapon).

The next building block is Environment. A first aspect of the Environment building block is Objects. Non-human entities play an important role in the scenario, from providing context and situational awareness (e.g., damaged vehicle in a car accident) to training on important skills (e.g., chemical spill introducing a new hazard). These objects may cover everything non-human that is virtually present in the scenario including, but not limited to, hazards, weather, furniture, personal items (e.g., cellphone), weapons, animals (e.g., dogs). These objects and where/how they are placed, behave (e.g., aggressiveness vs. non-aggressiveness), and are used in the scenario also introduce key opportunities for training, such as introducing visual ambiguity during decision making (e.g., an officer may have to distinguish between a flashlight and a gun in a subject's hands).

Another aspect of Environment is Audio. Realistic immersion often requires the presence of audio in the scenario beyond the speech of the avatars. Ambient noise, sound effects tied to objects and events (e.g., the sound of a fire, a dog barking) are all important for maintaining both realism and effectiveness of the training experience. The volume (or other properties such as balance and equalization), spatial properties, playback/pause, looping and choice of audio (including who can hear it) are all very important consideration. Additionally, audio can be used to intentionally inject distractions and stress for a user. Audio can either be programmatically controlled (e.g., sound generation and synthesis) or obtained from libraries of available sounds.

Another aspect of Environment is Visual. Like audio, visual effects and lighting are important for creating immersion and meaningful training content. These differ from the objects in that they relate to how something appears, such as a liquid spill looking wet or the embers and glowing light coming from a fire. The specific visual appearance and magnitude of such effects can change the scenario in ways that might be meaningful during training. For example, the color of smoke can be meaningful to firefighters and might change the implications of a given scenario. Additionally, visual effects can be used to intentionally inject distractions and stress for a user.

A next building block is Experiential and a first aspect of that building block is Haptics. Haptic feedback (i.e., touch) can be an important component to learning. Where and how it is introduced, including the presence and amount of haptic feedback, may be part of the content that is delivered by the system 200. This tangible content can be varied to alter a scenario and provide different experiences. For example, the experience of using a MR peripheral with no haptic feedback to control firing MR bullets during a training session would vary greatly compared to an MR pistol that provides recoil when fired.

Another aspect of the Experiential building block is Guidance. Training often provides some amount of guidance to the user, which guidance may vary by the type and level of training. This guidance may come from, for example, written instruction, direction from an instructor/trainer or even through the training interface itself (e.g., how a task report gets filled out provides some amount of guidance by presenting the information the user is expected to fill out, or how a user interacts with an object implicitly guides the user). When, where and how guidance is implemented can be a key part of training content. This aspect provides opportunities to elevate expertise by lowering the amount of guidance or remediate poor performance by providing more guidance. For example, a novice user may be presented with a detailed report interface to fill out, guiding them on what report information is expected. However, as the user advances, the form can become more limited with free form or audio response expected in place of the form. If the user has poor performance, the level of guidance in the form can be increased.

By programmatically generating a large library of various aspects for each of the content building blocks, the training content generated by ML3 can be varied automatically by combining these different aspects in different ways. These content building blocks are preferably generated and stored before the MR training experiences are created. Then, when a MR training experience is created, one or more of the content building blocks may be used in that content generation process. This allows for a diverse range of training experiences to be created merely by swapping one content building block for another content building block at any point in the content generation process or even at several points in the content generation process. This substitution process could be carried out intelligently (and automatically, via machine learning) to provide novel combinations of fundamental training experiences.

In some cases, this also provides the ability to by-pass the initial scenario identification/prioritization algorithms (ML1/ML2) entirely. When ML1/ML2 are bypassed (and at other times, including when they are not bypassed), the underlying first data source 102 can be taken as input for direct content generation in one of two ways: (i) use of the underlying data as prompts provided to ML3 for the creation of content that is based directly on that underlying data; and (ii) use of the underlying data as prompts to ML3, which serve as a basis for the generation of novel content or novel content combinations that may be created using existing libraries of content. This second method has the advantage of using only existing (and potentially vetted) content building blocks, and as a result is anticipated to be much faster compared to other methods where content is generated "on the fly."

In preferred embodiments, each of the algorithms used by the system 100 is or has the ability to be continually updated and to allow for the continual update to scenarios generated and the content (e.g., building blocks and aspects) associated with them. Preferably, these updates allow for the continual refinement and training of the algorithms themselves, which is important for enabling the creation of timely and relevant training experiences that capture the latest events and evolving situations that are relevant to users.

As such, the system 100 preferably also includes the training experience tailoring and optimization algorithm (ML4) mentioned above, which is configured to tailor and optimize MR training experiences previously generated by ML3. In preferred embodiments, this tailoring and optimization is based on information obtained from first data source 102, which is primarily an incident-centric source of data that relates to the incident itself and the contextual data that relates to that incident. However, the user's performance and biometric response to varying scenarios as well as the user's demographic information can also be consumed as an additional or second data source 104B as a user-centric data source that relates to the user and the user's response to training experiences. In certain embodiments, the second data source 104 may include user performance data 104A, user response data 104B, or user demographic data 104C, which are each described below.

User performance data 104A might include, as non-limiting examples, task-specific performance metrics (e.g., number of victims triaged in certain time frame, successful de-escalation or appropriate use of force, or accurate field treatment); adherence to strategy, tactics, or procedures in a scenario (e.g., following proper safety protocols, or maintaining the appropriate tactical formation); task, skill or other improvement compared to prior training (e.g., appropriate use of force in a scenario after previously showing inappropriate use for the same or similar scenarios); demonstration of skills, including showing proficiency in a skill, the ability to adapt a skill to a new situation, and the ability to create a new skill in response to a scenario (e.g., using sound firehose attack pattern for a given fire demonstrating mastery of a skill, using a firehose attack pattern for a new/different type of fire showing adaptation of a skill, or using the combination of multiple attack patterns for a dynamically-changing fire showing the creation of new skills).

User response data 104B is comprised, chiefly, of a user's biometric, physiological, and cognitive response to training experiences. However, user response data 104B is not limited to just data that is conventionally considered biometric, physiological, or cognitive data. For example, in certain embodiments, user response data 104B might include, without limitation: heart rate; breathing rate and oxygen levels; eye movement; pupil size; sweat; physical movement and biomechanical data (e.g., posture, skeletal motion data); facial expression and facial movement; speech and vocal sounds; or derived or inferred data (e.g., gaze fixation, eye saccade rhythm), current emotion, which might be inferred from facial expression or other biometrics, attention level, focus level, speech intonation.

Finally, user demographic data 104C might include information that is related to or that impacts a user but that is not directly related to their performance or their physiological response to training experiences. For example, user demographic data 104C might include data such as the user's age, gender, height and also other information, including the nature of the user's job (e.g., they are a firefighter or they are desk worker), their employer (e.g., FBI, SWAT, volunteer fire department), and their geographic location.

It is anticipated that, in at least some cases, the amount of data provided by the first data source 102 will often be significantly greater (i.e., a much larger number of incidents) than the data provided by the second data source 104 (i.e., a much smaller number of users). The reverse may also be true in other cases. Therefore, in certain preferred embodiments, in order to enhance the tailoring, the information provided by the second data source 104 may be weighted differently than other information provided by the first data source 102 in order to ensure that one data set is not "washed out" by another, larger data set.

Any of this data (i.e., the user performance data 104A, user response data 104B, and user demographic data 104C) might influence ML3's selection and generation of content. This type of data can be important for making training experiences hyper-relevant to the training needs of a specific individual, department or agency. By identifying what training scenarios users or organizations struggle with, the training scenarios can be appropriately prioritized and/or modified. Preferably, training experiences can be tailored and customized at any level or based on any divisible segment of the data provided to the system. As non-limiting examples, content may be tailored at the user level (i.e., adjusted for a specific user or in response to data related to a single user), at the agency/group level (i.e., adjusted for a specific group of user or in response to data related to a group), at a regional or geographic level (i.e., adjusted for a particular geographical region), based on a type of user (e.g., police vs. EMS), etc. Of course, depending on the division, some data might be relevant while other data might not be relevant. For example, a user's specific biometric response data might not be relevant when content is tailored for a specific geographical region.

In certain embodiments, this tailoring process might also include predicting other novel scenarios that trainees may struggle with but have not yet encountered (either in the real-world or in training), based on their past performance with other similar training scenarios. Additionally, those training scenarios that the users generally succeeds in can be modified to provide new scenarios that continue to challenge and raise the expertise of the users. Furthermore, by not strictly relying on the output of any other algorithm, training experiences can be customized by simply providing the necessary contextual prompt.

For example, understanding how well an individual is learning particular topics and scenarios, as well as whether that individual is ready to have new content/challenges introduced (and what to introduce), can require understanding the user's cognitive state. Thus, the user performance and response data 104A, 104B can be used to better inform the cognitive state of the user and to tailor the content to the user's skill level and mental/physical state in such a way that maximizes training effectiveness, such as increasing retention and understanding, and optimizes learning to ensure expertise is developed and maintained.

Training experiences may be updated at different points in time. For example, the updates might be provided after one training session and before a subsequent training session. In those cases, data from a particular user is preferably aggregated over prior training sessions and used, either individually or collectively, to recommend training content in subsequent training sessions. For example, after 3 sessions of good performance on single-car accidents, an EMT trainee may receive an accident scenario with multiple cars in their next session. In other cases, the updates might be provided in real time. In those cases, data from the user may be processed in real-time as it is collected during a training session and, optionally, combined with prior session data. The collected data is used to recommend training content changes in real-time that may be implemented within the same training session. This can include new content generation, where computing power permits, but also introduction of changes derived from a library of content. For example, if the EMT trainee is exhibiting good performance on a car accident scenario the car may suddenly start to leak gasoline that introduces a new hazard. In some cases these changes are made automatically. In other cases, the system 100 makes a recommendation of a proposed change that much be confirmed, such as by a supervisor or instructor, before it is implemented.

When a training experience is changed in real time, in order to seamlessly integrate the changes without breaking immersion (e.g., the scenario playing out continues seamlessly regardless of the changes made), the changes are preferably introduced at certain "injection points" within the training experience. Preferably, the MR content occurring before each content injection point is configured to enable a plurality of pre-generated MR experience content building blocks to be seamlessly substituted. This permits the MR training experience to be customized to provide a wide range of MR training experiences simply by substituting a first training content portion for a second training content portion at one of the content injection points.

These injection points can be pre-defined to occur at certain fixed locations or programmatically determined based on an algorithmic approach to each training scenario. For example, in preferred embodiments, adaptive meshing is used to tailor and optimize the training experience. The term "adaptive meshing," as used herein, means adapting the resolution (e.g., density and placement) of injection points dynamically as a training experience is carried out or progresses. For example, one might find a greater density of injection points (i.e., where changes to content are integrated) during certain segments of a training experience based on performance or response data, which data might be received either from the individual or from a group. A higher resolution of injection points might be useful, for example, in areas of a training experience where it is known (or learned) that user performance varies greatly and where a more dynamic (i.e., a more customizable) experience is needed to tailor or optimize performance.

In preferred embodiments, "adaptive meshing" of injection points into a training experience (i.e., the decision made by ML4 on whether, where and how to change the experience) may consider, without limitation, computing resources, timing, complexity, causality, or even plausibility of the change within the context of the scenario. For example, introducing a fire hazard in a car accident might occur only after gasoline has been released or spilled. The resolution of the injections may be broad (e.g., as a user advances from one "level" to the next, as one does in a video game), very refined (e.g., at the framerate of the content rendering), or event-driven (e.g., triggered on specific actions or events within the scenario).

Thus, in response to the data provided by data sources 102, 104, the present system 100 and, in particular, ML4, preferably generates updated content. In other cases, ML4 provides a recommendation to ML3 to generate updated content, preferably including the changes that are needed, which would be used in the next training portion, cycle, iteration, injection point, etc.

Section 2: Geometric Mapping & Occlusion

Figure 2:
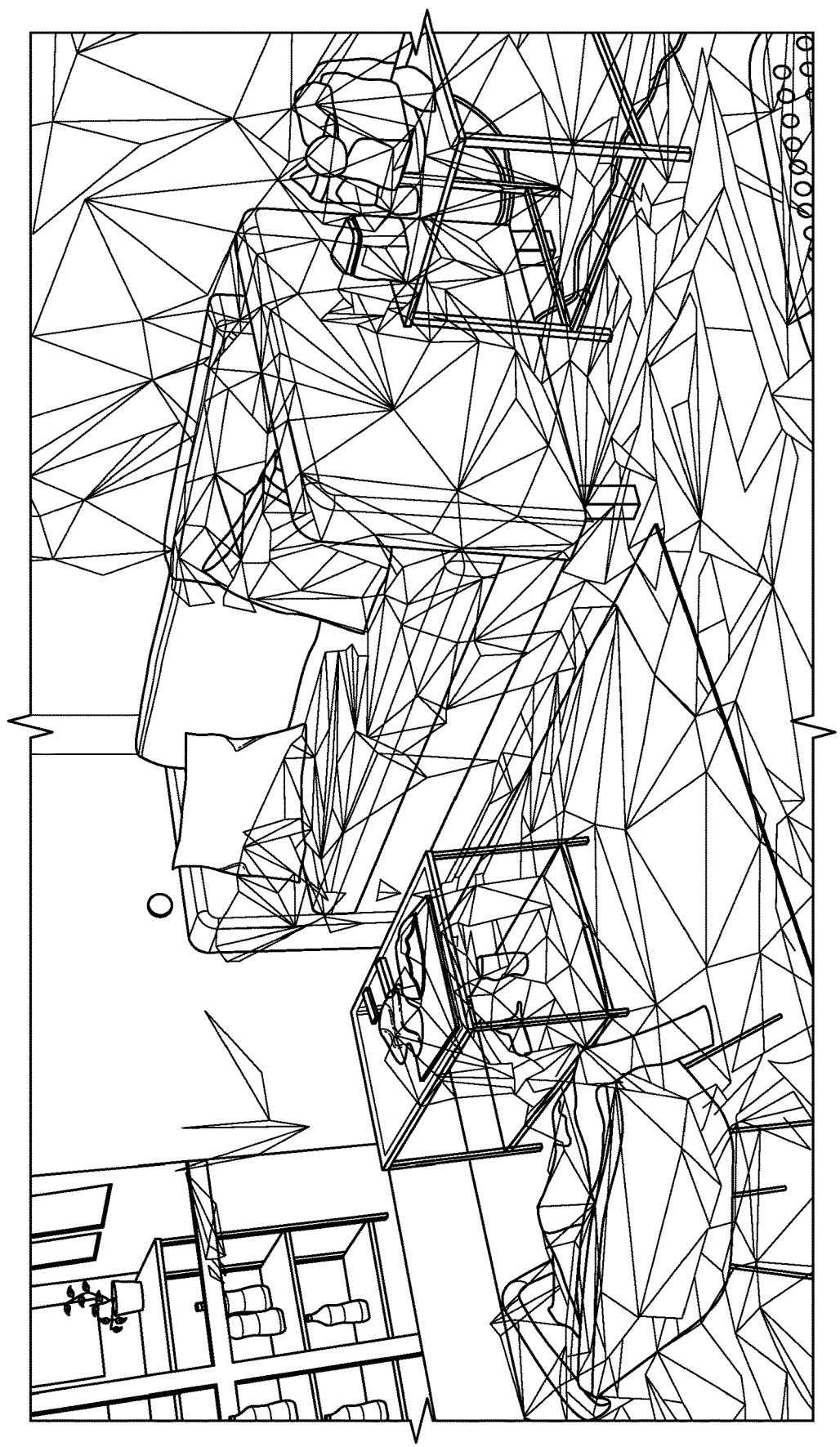
FIG. 2 depicts a digital mesh of polygons that is conventionally used to identify visible surfaces that are then translated into a virtual representation used to interact with digital content.

After the MR environment and content is created, interactions within those environments do not take place entirely within either the physical or virtual worlds, but a combination of both. MR systems employ a knowledge of a user's physical surroundings to provide immersive interactions with virtual content by performing "meshing" of the environment to identify physical objects. This meshing occurs using a variety of sensors, from RGB cameras to infrared time-of-flight systems and LiDAR. As shown in FIG. 2, these systems create a digital mesh of polygons that identify visible surfaces, translating those surfaces into a virtual representation that can be used to interact with digital content. In general, meshing is a necessary component of MR systems to provide safety (e.g., alerting a virtual reality player when they are about to collide with a wall or piece of furniture) as well as incorporating the physical surroundings into physically realistic simulations via a process called "occlusion," which is one of the most important factors in creating realistic augmented or mixed reality interactions.

Figure 4:
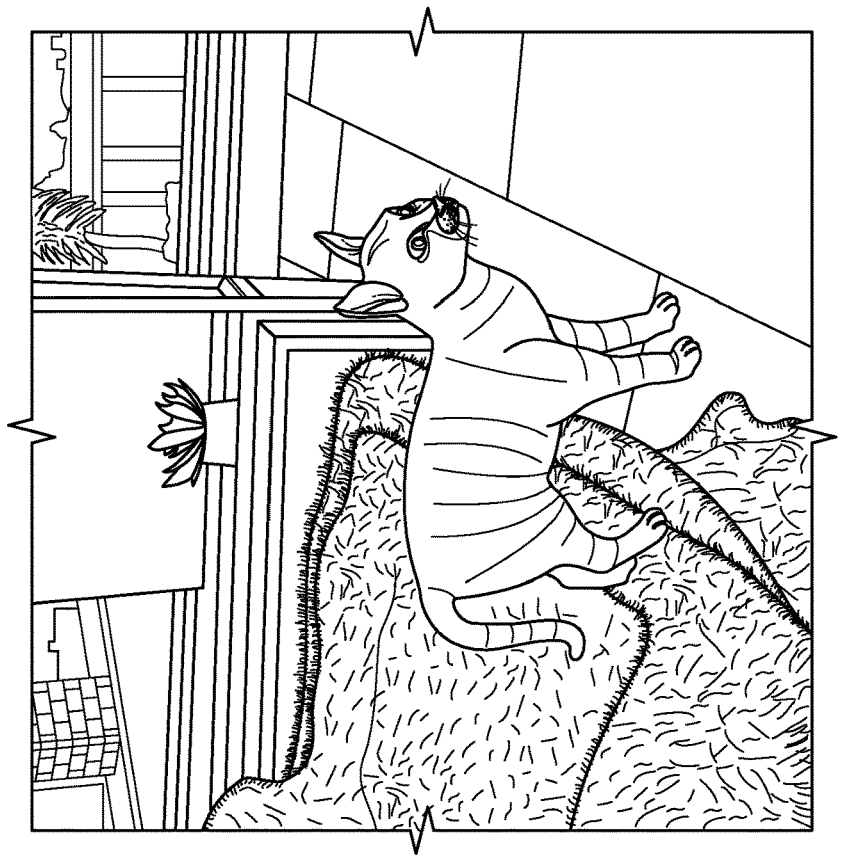
FIGS. 3 and 4 depict an MR environment having a computer-generated cat standing behind an actual, real footstool with and without appropriate visual occlusion, respectively.
Figure 3:
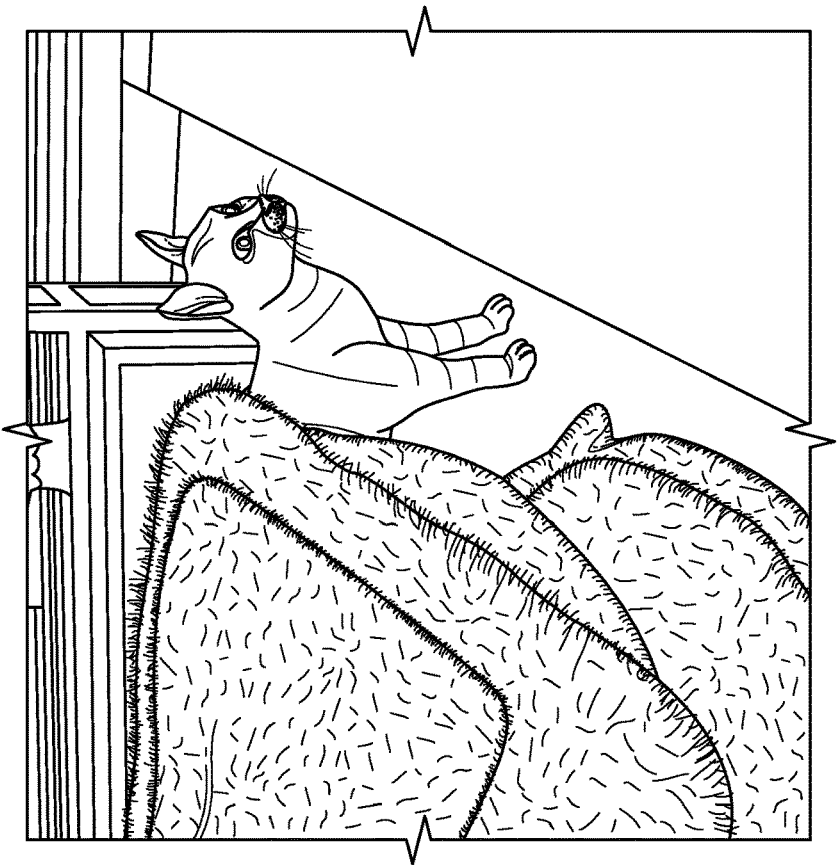

Occlusion is the visual blocking or obstructing of an object. That is, light emitted or reflected by an object is blocked from reaching the visual receiver (e.g., the human eye or a camera). For example, a human walking behind a wall becomes occluded to those on the other side of the wall. Similarly, a person becomes partially occluded when walking behind a couch. In MR environments, immersion is broken and realism is reduced when physically-realistic occlusion is not present with digital content. For example, a digital avatar represented in MR content that walks behind a physical couch should be partially occluded by that physical object. In other words, the lower portion of the person's body should blocked by the couch and should not be visible to others located on the side of the couch opposite the person. The failure to correctly occlude breaks immersion and reduces or removes entirely realism. With reference to FIGS. 3 and 4, an MR environment is shown that includes a computer-generated cat standing placed into a scene that includes a real physical object (i.e., a footstool). In FIG. 3, the cat has been appropriately occluded, such that it appears to be standing behind the footstool and its hind legs are hidden from view. On the other hand, in FIG. 4, the computer-generated cat is not properly occluded and, for that reason, appears to be standing partially on the floor and partially on the footstool, which creates an unrealistic appearance.

Most MR systems provide realistic occlusion via meshing (e.g., the couch becomes represented as a surface of digital polygons). For example, 3D scans of physical spaces have been made using dedicated scanning systems (e.g., LiDAR-based scanning cameras, such as on the iPad Pro or the Matterport Pro2). The scans captured are then exported from the scanning device and used to create 3D meshes of the scanned area for use in MR content. However, meshing is a complex procedure that can be both computationally and memory intensive for an MR system. While there are certain devices that claim to provide high-speed, real-time meshing, with meshing updates on the order of 10-20 ms, the vast majority of devices provide real-time meshing on a timescale of several seconds. This timescale is much slower than cognitive or physical timescales of the user and their interactions. For stagnate surfaces, such as walls and furniture, these longer timescales can be appropriate. However, these timescales are not suitable for moving objects (e.g., doors opening, other humans, etc.) or for when the user is moving rapidly into new locations (e.g., moving quickly from one room to the next).

Meshing is further limited by the computational power and memory capacity that it demands. As a result, the physical volume that can be meshed is often limited (e.g., ~10 meter per dimension of a cubic volume). This limitation, of course, limits the size of MR environment that can be utilized and meshed. While mesh caching and updating can be used to overcome this limitation to certain limited extents, it results in the same timescale problems noted previously.

Environmental conditions can create even further limitations on the meshing. For example, certain sensors used in the meshing process do not recognize surfaces with reflectivity that is either too low (e.g., black or dark-colored surfaces) or too high (e.g., smooth metal floors), especially if the sensors are positioned at an incorrect or less than ideal viewing angle. Low light or a lack of visual features (e.g., smooth, white walls), as well as surfaces that are too close to or too far from the sensor can also result in meshing failures. None of these conditions are particularly rare in real-world environments and, in combination with the other previously-described limitations, can combine to result in meshes that are incomplete (i.e., have holes or large missing sections). Holes in meshes are problematic for a number of reasons, including because such holes would be permit for situations like that shown in FIG. 4, where the cat is improperly occluded, to occur.

Figure 5:
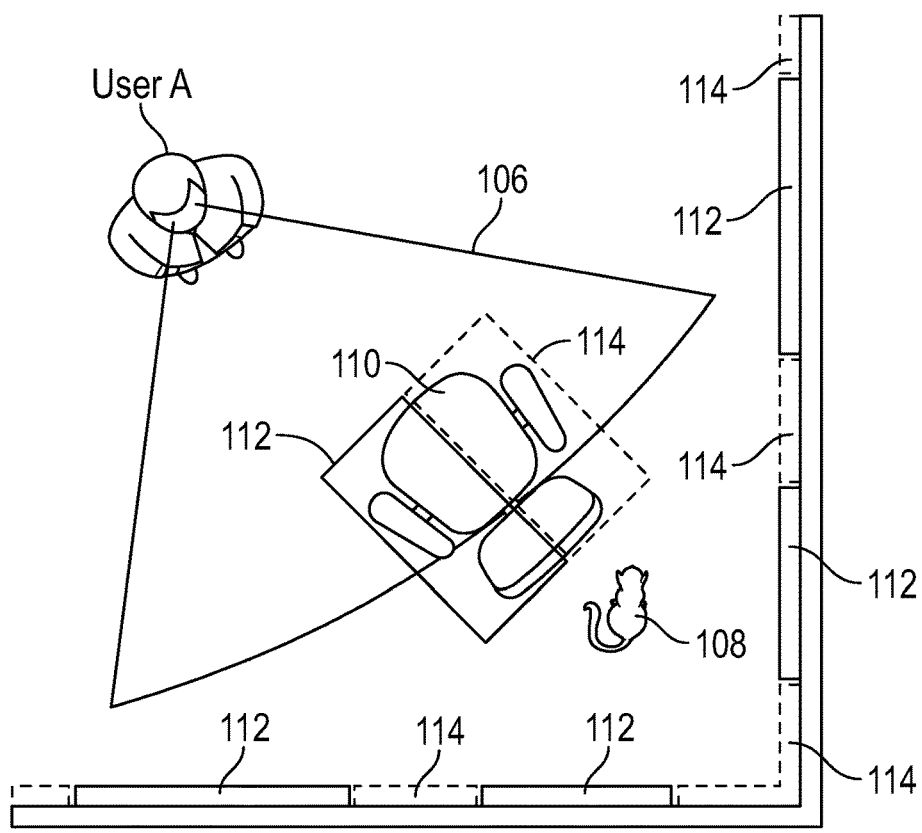
FIG. 5 depicts a user standing in a room and viewing a virtual environment where the mesh includes holes that produce improper visual occlusion.

Another example is shown in FIG. 5, where User A is located within an actual room and, through the use of an MR peripheral (not shown), such as googles, glasses, etc., sees (as illustrated by vision cone 106) and is able to interact with simulated content 108, such as a simulated cat located behind a real chair 110, that is projected on or located within the actual physical location. The simulated content 108 could, of course, be anything or any kind of character or scene or environment. In each case, for the reasons discussed above, it is important to provide an effective digital mesh 112 in order to ensure proper occlusion. If the scanning process was faulty or incorrectly performed, holes 114 may be located within the mesh. At each of these holes 114, the virtual content provided would not be properly occluded and the virtual content would not be presented or interact with the actual real-world environment correctly in those locations where holes 114 are located. For example, since the virtual cat 108 is located behind the chair 110, it should be hidden from User A's view. This would be the case in those locations where the digital mesh 112 has been correctly created (i.e., the left side of the chair, as shown in FIG. 5). However, the cat 108 would be incorrectly visible on the right side of the chair (as shown in FIG. 5) due to the hole 114 in the mesh. In another example, if User A were to "throw" a virtual ball at the wall, the ball would correctly bounce off of the wall in those locations (i.e., wall sections 112), where the mesh is created correctly. However, the virtual ball would pass through those locations (i.e., wall sections 114), where holes are in the mesh.

These types of failures of the simulation would, of course, drastically reduce the overall realism of the simulated experience. This problem is particularly pronounced in tactical training for first responders. These training scenarios involve large physical spaces (e.g., entire office buildings) in which the user is moving rapidly across large distances. Simultaneously, realism and physical fidelity are paramount to the training experience and effectiveness. The effect of lost occlusion results in loss of realism and physicality when it is needed most. For example, a police officer training on an active shooter event using an MR peripheral may experience "x-ray vision" if the walls do not properly occlude an adversary in a different location of the building. Not only does this remove the immersion necessary for effective training, but it removes the physical realism often necessary to train critical skills (e.g., looking around a corner, or hugging a wall prior to clearing a room).

In order to prevent these types of failures, specialists are often used to perform the scanning process. Unfortunately, the scanning systems require a non-negligible time commitment to perform the actual scanning process and also require that the locations being scanned to be free of other people, etc. Thus, the scanning process may require a significant time, cost, and personnel investment and a coordination of schedules and may, even then, cause a disruption to building or company operations.

Figure 6:
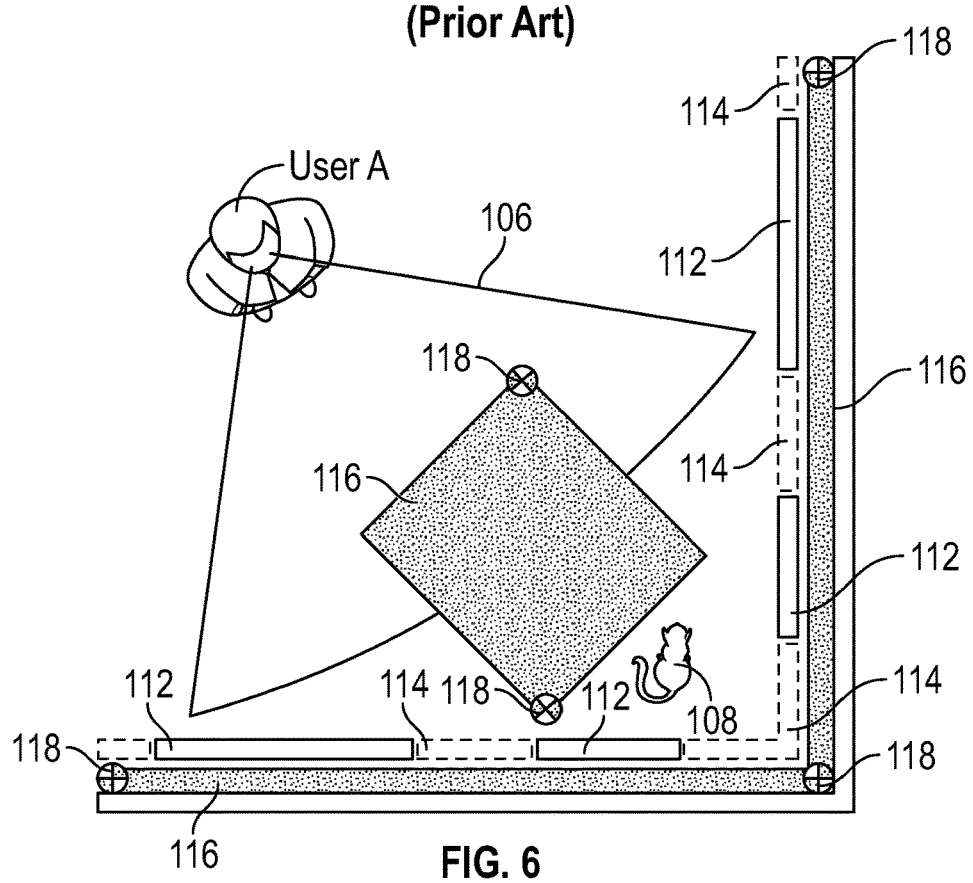
FIG. 6 depicts a user standing in a room similar to FIG. 5 but where the holes are "patched" by an occlusion fallback according to an embodiment of the present invention.

With reference to FIG. 6, the present disclosure provides systems and methods for (1) providing an "occlusion fallback" 116 which is essentially a backup mesh used to patch holes and to replace missing parts of meshes generated by MR peripherals (also called "primary" meshes) and (2) for enabling digital environments to be created much more quickly, easily, reliably and using fewer computational resources than was previously possible. Occlusion fallback can be used to ensure the user's physical environment properly occludes virtual content and that it creates a realistic MR experience. However, the occlusion fallback systems and methods disclosed herein can be used exclusively as well. In other words, the presently-disclosed systems and methods for creating meshes may be used without the need for a primary mesh to be generated by an MR peripheral or requiring scanning by a separate tool. Advantages of these systems and methods are that they guarantee virtual content is occluded regardless of the performance of the MR peripheral that generates the primary mesh. Additionally, these systems and methods avoid real-time meshing issues and also memory and performance limitations by leveraging user-placed geometric "primitives" to approximate the physical environment.

The present disclosure provides two exemplary ways in which an occlusion fallback 116 may be provided, but any other methods may be used for carrying out the general concept of providing a backup mesh that supplements or reinforces a primary mesh.

In a first method, a user utilizes the target location itself to provide the relevant geometry. According this method, the user marks or tags a series of geometrically-paired locations in their physical environment while wearing a MR headset. The general "tagging" process is known in the art. For example, in certain tagging processes, a user will position an MR headset or peripheral in a selected location and then take some sort of action (e.g., pressing a button on a controller) to identify and save that location in space to the MR system. Generally the order of tagging does not matter. However, in certain cases, it may be desirable or even necessary for locations to be tagged in a certain order.

From this tagging, the occlusion fallback is created. Preferably this is accomplished by tagging geometrically paired locations to define geometric primitives, which are then used to define portions of the mesh. As the term is used here, "geometrically-paired" means two or more locations that are paired together or associated with one another in order to define a geometric primitive or some other shape or defined portion of the mesh. The term "geometric primitive" refers to primitive geometric shapes, such as planes, cubes, spheres, cylinders, and the like, that can be placed into a mesh in order to define some similarly-shaped physical object in that space (e.g., a cube may be used to generally represent the a table or the footstool shown in FIG. 3). Thus, according to this method, by using just a pair of location-sensing tags, two locations can be paired together to define the length of a plane in the horizontal dimension.

The pairing can be defined prior to or after tagging locations. For example, through the use of a computer interface, a user might select two QR codes or serial numbers to pair together or to associate with one another. Then, those QR codes (or serial numbers) are associated with a pair of markers 118 that are placed at appropriate locations for tagging. This is an example of the pairing process occurring prior to the tagging process (i.e., the process of placing the markers). Alternatively, the pairing process can be carried out after the tagging process. For example, using a computer interface, a user might see various tagged (but unpaired) locations that were previously marked (i.e., tagged) using a peripheral device, such as a controller. The user might then select two or more of those marked locations and associate them together in order define a specific portion of the mesh (e.g., two marked locations are paired together to define a wall, two marked locations are paired together to define a cube). The tagging process may also be carried out with any of the MR peripherals or even an MR headset, or it may be done by logging the location and orientation, QR codes, or Aruco codes via the device cameras, etc.

The mesh is not necessarily created during this tagging procedure and can, instead, be created at a later time following the tagging procedure. However, in most cases, wearing or carrying the MR headset or an MR peripheral is necessary to ensure the tags' 118 relative positions and orientations are captured in the coordinate system of that device. Additionally, the tagging procedure need not be done on the same device that the content will ultimately be loaded in because the relative locations can be shared across multiple devices. For example, the tagging process might be carried out by one dedicated "tagging" headset and then shared with others. In other cases, tagging might be carried out using another non-MR peripheral or headset, such as a tablet or a headset from an entirely different platform. In each case, the key to the tagging process is that the position and orientation in 3D space is accurately tracked.

Next, in the example given above, where two tagged locations define a plane for representing a wall, the height of the plane is assumed. For example, a pre-defined or standard wall height might be assumed that can then be overridden by a user as needed. These two locations, thus, define the length of the wall and a virtual occluding plane (of the assumed/ predefined/overridden height) can be automatically generated between them without relying on meshing. In other cases where the height of the wall matters, such as a half-wall, two options are available. First, the two locations identified by the markers 118, which determine length, may be encoded with knowledge that the vertical position of the tag itself is meaningful in defining the height of the plane. For example, the marker's vertical location may define the upper (or lower) limit of the plane. Of course, the markers 118 can be encoded to understand that its position is relevant in any direction (i.e., the tag's location may be used to determine max/min height or max/min width). The second option is to make use of a third location to explicitly define the plane in both the horizontal and vertical dimensions. In addition to walls, this same method can be used to define any physical environment that can be decomposed to a set of planes, such as floors.

In addition to planes, other shapes can also be developed by pairing two or more locations (e.g., each point of an octagon). Additionally, a lesser number of locations may be used to create certain pre-defined shapes where sufficient assumptions are made. For example, two points can define opposing corners of a square or rectangle having 90 degrees corners and an assumed/predefined height. For example, as shown in FIG. 6, the chair from FIG. 5 may be represented in the in the mesh within the virtual environment by placing markers 118 at opposite corners of the chair. In turn, in the mesh for the simulation, the chair might be represented as a rectangle that extends upwards (i.e., out of the page, as viewed in FIG. 6) to some predetermined height.

In other cases, the user may select and place pre-defined virtual geometric primitives or other pre-defined virtual shapes in a particular location in order to account for objects in the physical surroundings (e.g., tables, chairs). The purpose of this method is to simplify the definition of objects without requiring paired locations. While geometric primitives are not exact replicas of the objects, they are sufficient for creating realistic occlusion. More complex virtual objects could be placed, beyond geometric primitives, if necessary. But even in the case of placing, for example, an actual virtual table the virtual models can be designed to optimize performance with minimal polygon count.

Figure 7:
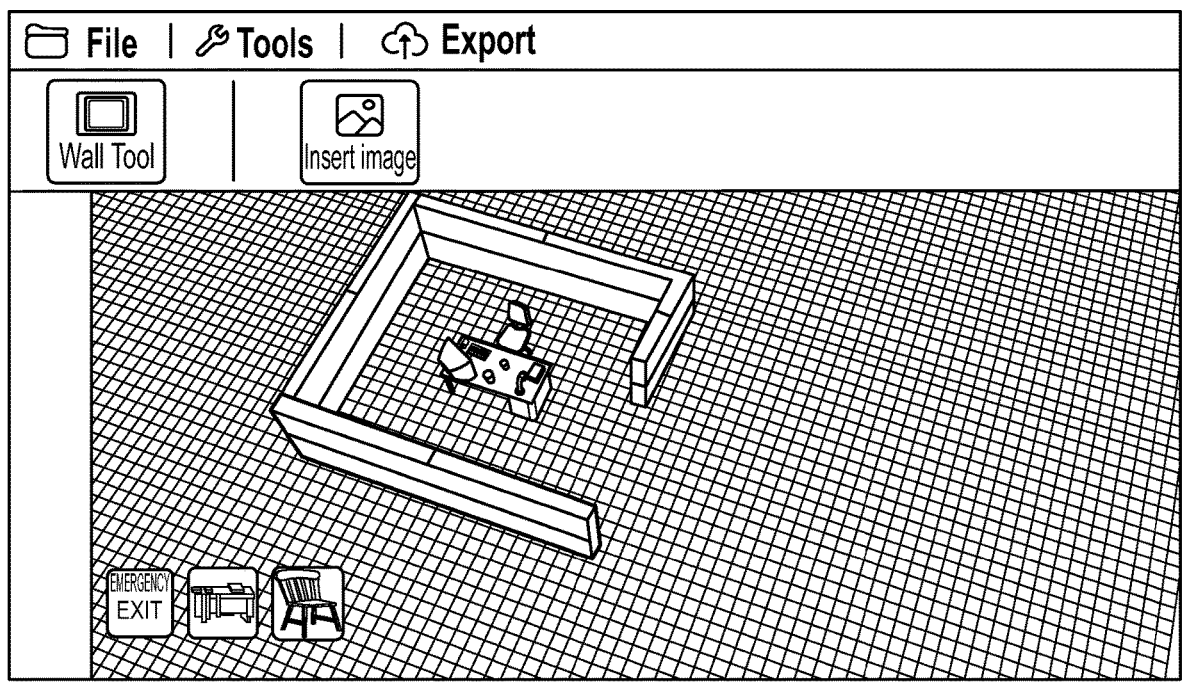
FIGS. 7 and 8 depict standalone interfaces for placing geometric primitives and other virtual object models into a computer-generated space.
Figure 8:
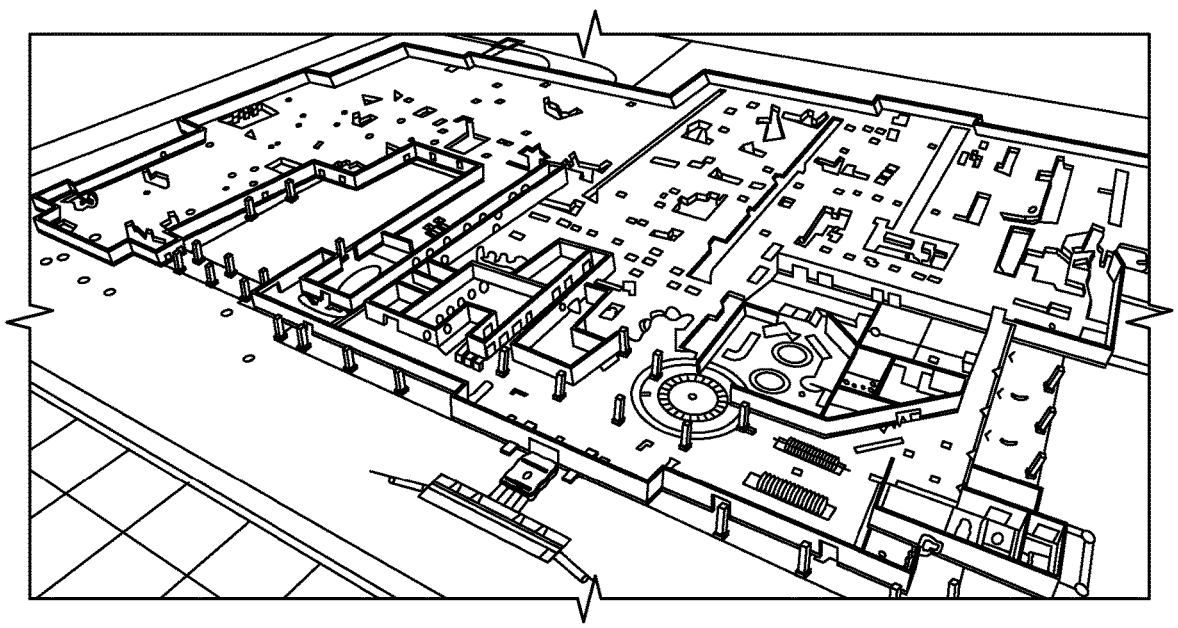

In a second method, the user need not be in the physical space at all. Instead, as shown in FIGS. 7 and 8, via a computer interface 160, the user places geometric primitives and/or other virtual object models 162 into a computer-generated space 164. The interface 160 serves as type of mapping application, in which the user draws the physical space in 3D, including any walls, doorways or relevant objects. The interface 160 can support multiple floors, including staircases, which are necessary not just for occlusion but A.I. navigation and physical interactions in multi-level spaces. This "standalone" interface 160 is device agnostic, requires no external sensors, and may be implemented on any computer device (e.g., PCs, tablets, etc.). Advantageously, when using this interface 160, a user can import an image of the desired layout (e.g., a fire plan layout or architectural drawing) to guide their development of the virtual space 164. In addition to defining the structure and objects present in the space 164, this interface 160 allows the placement and definition of training exercise-specific items, such as A.I. entities (e.g., adversaries, bystanders and victims with particular dispositions), hazards (e.g., fire, chemical spill, explosion) (not shown).

The two methods described above may also be merged. In particular, the "map drawing" aspect of the second method may be performed from within the MR headset utilized in the first method. This can hybrid method can provide a more user-friendly way to create the virtual environment, especially in those cases where measurements of the physical structure are not available and where there are unique objects/structural features that are not readily approximated by geometric primitives or other pre-defined digital models. For example, the user may provide several points of a complex surface (e.g., using QR codes, or by marking the points with a peripheral) to effectively define individual polygonal masks to define an oddly-shaped object located within the space. Additionally, this hybrid method would further permit a map that was initially created in the standalone application (using Method 2) to then be loaded into an MR headset for more detailed editing and refinement. The reverse is also true, where maps defined in an MR headset could be refined in the standalone application, or a map iteratively worked on between the headset and the standalone application.

In still other cases, this system and method permits occlusion objects and visible virtual objects to be loaded into the generated map. In many cases, a building may be entirely unavailable for training (e.g., due to logistics). SWAT personnel frequently train on raiding buildings for which they are only provided a simple sketch of the interior layout. Their current training approach is to draw the layout in chalk on the ground and practice tactical maneuvers. Using the method above, these types of simple sketches could be quickly placed into the mapping application and a fully virtual, 3D floorplan could be quickly created for training. With variations on placing objects and wall positions, this would allow for rapid rehearsals on multiple scenarios even when a physical location is unavailable. Similarly, firefighters may perform similar size-up and search and rescue training on user-defined structures. Even within a physical location, such a capability would allow for changes to the training to simulate new scenarios, as described in Section 1 above, such as by placing virtual walls in certain areas to simulate closer quarters or placing obstacles that might not be physically present but are meaningful for training on potential scenarios.

In general, the approximation provided by the occlusion fallback processes described above is not a perfect representation of the physical object and it generally has a lower fidelity to the true physical structures when compared to the polygonal meshing provided by an MR peripheral. However, even with these limitations, the fallback mesh provided is more than sufficient for providing realistic visual occlusion. Additionally, an advantage of using geometric primitives drastically reduces the number of polygons that must be rendered and held in memory. This allows for extremely large spaces to be captured and digitally represented, which generally is not possible when such environments are scanned using MR peripherals according to conventional methods. Furthermore, the geometric nature of this approach allows for a massive simplification of the user's interactions with the MR system when compared to similar interactions with an external scanning camera (e.g., Matterport). Further, the present system and method is highly fault tolerant and requires almost no training or experience to use successfully. By not relying on meshing at all, this method avoids the issues associated with scanning processes, such as those discussed previously. The first method mentioned above allows the user to walk quickly through a space while identifying and marking a few key locations (e.g., two ends of a wall) to fully define the space. The second method described above allows the user to quickly define the space even if they are not located in the space at all.

In each of the methods described above, the position and orientation of occlusion objects (e.g., geometric primitives or otherwise) and virtual objects placed within a map is stored relative to a defined anchoring position. This anchoring position allows the maps to be loaded on any device, regardless of that device's internal coordinate system. The virtual map is then aligned with the physical surrounding by using shared, physical world anchor points as physical fiduciaries, as discussed in the "Spatial Alignment" section below.

Section 3: Tracking & Anchoring

Next, realistic interactions between users and also between the user and their environment are important for creating and maintaining realistic and immersive experiences with MR content and devices. For example, correctly representing the motions and interaction of soldiers moving, as a unit, through a building can be important for training those individuals on correct techniques. The appropriate techniques in such a scenario might require, for example, understanding each person's location, posture, gaze, etc. In addition, tactile and haptic feedback has also demonstrated substantial benefits for understanding and retention. For example, an immersive MR experience for firefighters benefits dramatically from allowing the user to incorporate the use of an actual fire hose nozzle in the environment. An actual nozzle provides realism unavailable in virtual representations of the equipment, such as the weight, "feel," and maneuverability of an actual fire hose nozzle. However, the objects and equipment that would ordinarily be used by users in carrying out real world tasks, such as actual fire hose nozzles, are not provided with means for direct tracking by MR systems. While certain prior art systems are able to track objects within a uniform coordinate system, the tracking process becomes much more difficult when multiple coordinate systems are used. Multiple coordinates might be used when multiple users are interacting with the same training experience using different MR headsets or devices. Another issue is that many conventional training simulators fail to provide means for using real-life equipment, such as a real fire hose or a real pistol, in MR training experiences. The presently-disclosed system and related methods address these and other similar issues found in the prior art that are related to tracking objects in in MR environments and related to providing realistic, tactile and haptic feedback to users.

Object Tracking

In order for a user's interactions within an MR environment to be tracked and in order for that environment to be responsive to those interactions (e.g., including correctly representing the position of objects, such as the user/player, device MR peripherals, or other items, such as furniture or other objects located at the user's location, or other users), the objects and users must be correctly tracked within a given environment. This can require the MR system to continuously construct and update a map of the environment in real time, while simultaneously keeping track of the tracked objects' and users' locations within that environment. Often, in constructing the map of the environment, MR systems generate a mapping coordinate system (e.g., orthogonal x, y, and z planes), and the locations of objects within the space are assigned or mapped to a specific location within mapping coordinate system that may be updated over time. This creates a "mapped" environment that includes mappings of locations for objects within the MR environment. Once that mapped environment is created, virtual or generated experiences can then be provided within and interact with the environment.

This system is configured to use various methodologies for tracking objects in space. Illustrated below are examples of tracking objects in space. However, other methods may also be utilized for this purpose. First, image tracking can be used. One problem associated with certain MR systems is that they sometimes limit the total number of MR peripherals that can be connected and tracked. For example, some headsets are limited to a single peripheral. In those cases, image tracking might be a useful in place of or in addition to tracking MR peripherals. This system is configured to use image tracking technologies, such as visual odometry, wherein the translational and rotational motion of the objects being tracked, including the users of the system and objects within the system, is estimated using optical or electromagnetic means (e.g., mono, stereo and LiDAR cameras). Using visual odometry, feature-based methods extract image feature points (e.g., tokens or pixels) of an object of interest and track them over a sequence of images. These image tracking methods use an algorithm, such as the conditional density propagation or "condensation" algorithm, to track the movement of an image from a camera. This can be accomplished by attaching and tracking a defined image that the MR system knows to track to the object of interest.

Image tracking, however, is not the preferred method for tracking objects in space because it has been found to be somewhat unreliable. The accuracy of the frame-by-frame analysis of movement is subject to visibility of the tracked images or features and incurs high computational overhead that is often impractical to run with high-fidelity and real-time updates on an MR system. Furthermore, the tracking itself often experiences substantial drift due to uncertainty in the image tracking methodology and instrumentation. Additionally, drift is likely to be exacerbated by some viewing angles and lighting, depending on the camera's characteristics. Frame-over-frame uncertainty will tend to increase the longer visibility of the image is not under ideal viewing conditions. Additionally, tracking is completely lost when the image is fully obscured.

For those reasons, an alternative option for tracking objects' movement and position in space is through the use of inertial measurement units, accelerometers, or gyroscopes (collectively, "IMUs"). Preferably, one or more Bluetooth-enabled IMUs or non-Bluetooth IMUs combined with other Bluetooth-enabled electronics are connected at any convenient location to an object of interest that the user wishes to track and are configured to communicate data to the MR system.

IMUs are capable of detecting and reporting the rates of change of objects of interest. However, with only a single IMU, there may be some uncertainty in the accelerations detected. Therefore, in preferred embodiments and in order to reduce this uncertainty, at least two IMUs that are constrained by a rigid body, each with a minimum of six degrees of freedom (6DOF) consisting of acceleration on three translational and three rotational axes, is provided. An example of an IMU that is suitable for this application is the BerryGPS-IMU that is sold by Ozzmaker. Additional IMUs be used to further reduce tracking uncertainty or to provide tracking of other parts of the object that may not have a rigid body attachment to other tracked parts of the object (e.g., two IMUs may be placed on either side of a mechanical joint).

The locations of the IMUs on the object are defined in the MR system. Preferably, the system is told exactly where the IMUs are mounted to the object being tracked. For example, if an MR system generates virtual water coming from a fire hose nozzle and the nozzle is tracked by an IMU placed on the bottom of the nozzle handle, the system is preferably told that the IMU is attached to the bottom of the handle. Additionally, the dimensions of the nozzle are provided to the system in order to generate the virtual water from the appropriate location on the nozzle.

The IMUs are preferably mounted at mounting locations having a rigid body constraint with the object whose motion is to be tracked. In other words, the IMU and the object that is being tracked are in a fixed (i.e., rigid body) arrangement. This helps to ensure that the system mechanics are deterministically solvable. Using a rigid body attachment is also important for allowing the measurements of each IMU to be transformed into a surrogate measurement for both other IMUs and the overall composite IMU system. These complimentary measurements can then provide a system of constraints on the composite IMU system, decreasing the overall uncertainty that will allow for a more precise measurement of position and rotation. An example of a suitable rigid-body system that may be used is a skeletal or "root bone" system, wherein the movement and position of a multiple-IMU system is constrained or is defined as a series of jointed rigid bodies originating from a single "bone" having a known position and orientation. This bone is a theoretical construct and while it may coincide to an actual skeletal bone, it need not be based on an actual bone.

For example, if it is known that the device being tracked will always be held in the hand of the user, this knowledge can be used as a constraint on the position of that object based on the limited motion available to the human hand and arm. Similar approaches are used for 3D position tracking in accelerometer-based motion capture suits, such as the Rokoko Smartsuit, where accelerometers placed at various points on the body alongside a defined skeletal model provide the necessary constraints for robust 3D tracking of human motion.

When using this method, external data or assumptions are necessary to define the skeletal model. For example, the MR headset provides a known location of, for example, a user's head. Based this fact, this location can be treated as a root bone from which the rest of the skeletal model may be built even though not all physiological bones are directly connected to the human head.

In the case of multiple IMUs, such as motion capture suits, the skeletal model may be defined by inputting the height of the user. Typical human proportions are then used to assume the rest of the skeletal model (i.e., arm length, leg length). The relative motion of the several IMUs can then be constrained to the assumed rigid body of the skeletal model and reduce the uncertainty in the calculated position. The Root Bone system of constraints can be particularly powerful when assumptions on user behavior are reliable. In fact, in some circumstances, full 3D tracking of the object can be achieved with the Root Bone methodology even when only the orientation, and not the position, is known.

Preferably, the IMUs are provided with onboard or embedded Bluetooth, either in the same circuitry or provided with a separate microcontroller or microcomputer, such as an Arduino or Raspberry Pi. An advantage of the use of Bluetooth-enabled IMUs is that they can be configured to interact with other Bluetooth electronics, such as switches or buttons, to provide additional interactions with real-life objects (e.g., fire hoses or pistols). This would, of course, allow these real-world objects to be used by users in interacting the MR experience. For example, pressing a Bluetooth button connected to a real-life fire hose could cause generated water to put out a generated fire.

The IMUs are preferably configured to collect and transmit telemetry data that includes translational and rotational acceleration along different axes (e.g., typically six axes, three translational and three rotational) to the MR system. This telemetry information can then be used to reconstruct the relative position and movement of the object within the mapped environment using kinematics. For example, the following kinematic equation provides the position of an object in the x dimension given the acceleration a as a function of time along that axis where $x_0$ is the required point of reference:

$$x = \int_{t_0}^{t} \int a(t) + x_0$$

The IMU data (i.e., the acceleration in various dimensions) described above can only reconstruct relative positions, rather than absolute position, in a given space and, thus, require some point of reference for the origin. While this might be sufficient with some assumed point of origin that is common to all such devices, a tracking problem arises when relative points of origin for various objects cannot be determined and tracked. For that reason, as discussed below, this system also advantageously provides an anchoring process whereby "anchors" are established for allowing the MR content existing in multiple different coordinate systems to be associated with one another through their shared association with real world anchor locations. This, in turn, allows the movement and position of those objects to be tracked across the various coordinate systems by the MR system.

It is further noted here that the placement of additional IMUs on a rigid body with known relative locations can substantially reduce the uncertainty in a(t) of the total system. With IMU sizes sufficiently small being available, a tracking device can be implemented consisting of a rigid body with multiple IMUs attached. For example, a solid metal, equilateral triangle could have one IMU at each point. This, in effect, creates a composite IMU system whose acceleration (and, therefore, position and rotation) may be more accurately determined based on all of the data received from all the IMUs in the system.

Spatial Alignment

Figure 9:
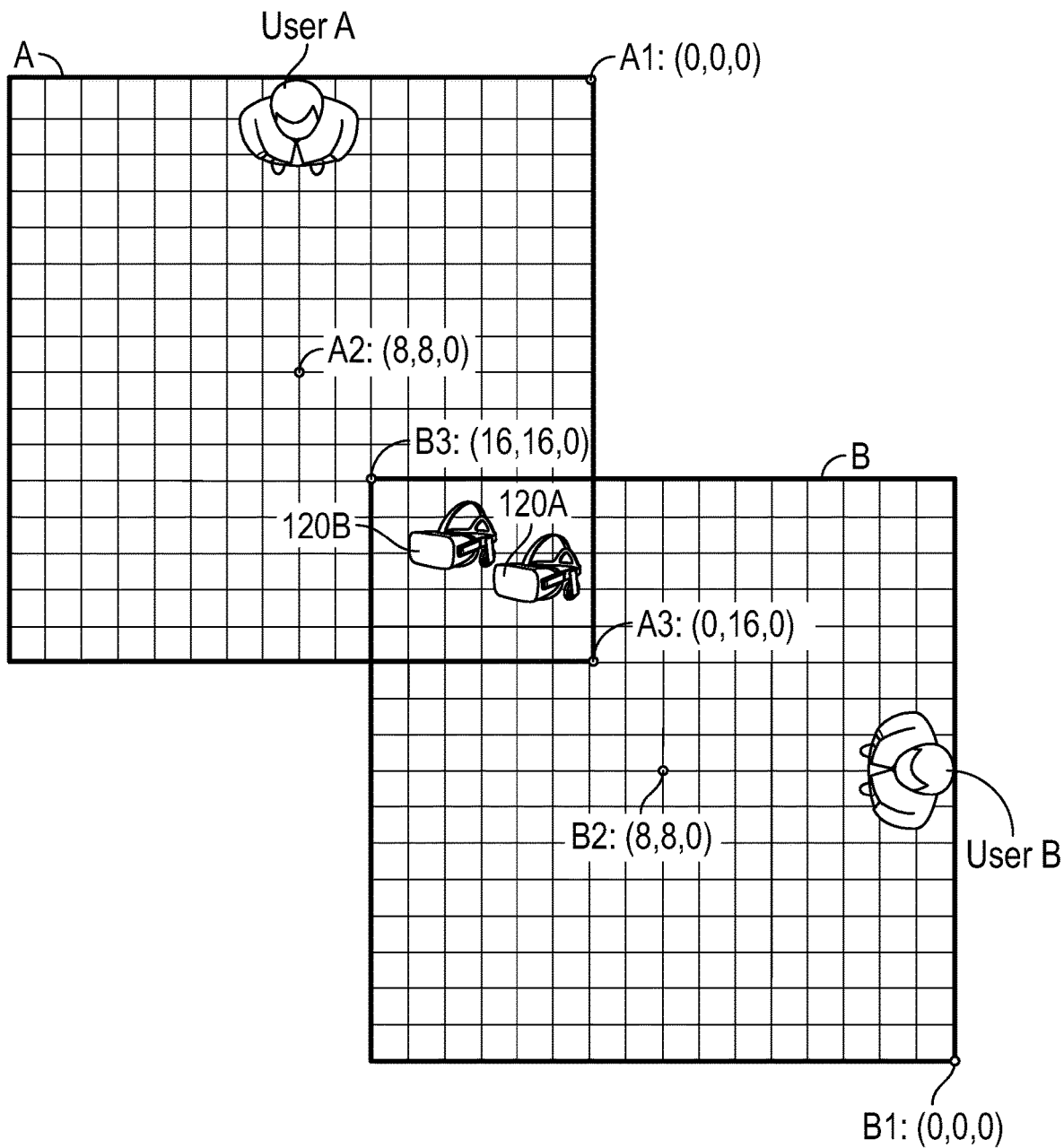
FIG. 9 depicts two conventional mapped environments that utilize different coordinate systems and map origins.

Next, even if users and objects are correctly tracked within their own coordinate system, the tracking may be incorrect in other coordinate systems. To illustrate the problem, in FIG. 9, two players (i.e., User A and User B) are shown and each is provided with a different MR environment (i.e., MR environment A and B, respectively) that is each provided with a different coordinate map having a different origin (i.e., 0, 0, 0). A pair of MR headsets 120A, 120B are located within environments A and B. In addition to tracking the origin location (i.e., 0, 0, 0) with respect to the physical world, MR systems may also be tasked with also tracking each MR peripherals (e.g., an MR pistol, not shown) and MR headsets (e.g., headset 120) used within the MR environment as well as the relative position of those devices within the MR environment. If the coordinates associated with MR headsets 120 are not correctly translated between those headsets and their respective MR environments, the movement or position of Users A and B and characters within their respective environments might be incorrect or their motion might be incorrect (e.g., leftwards movement of an MR character might be incorrectly generated as rightwards movement for certain users). While this is a problem in VR environments, where all content seen by users is generated, the problem is much more pronounced in AR environments, where only a portion of the content is generated. As an example, in AR environments, users of the system might be visible to other users of the system. If the tracking of the users is not correctly calibrated, one of the users (e.g., User A) might be, subjectively, looking "down" at the ground while, at the same time, appearing to look "up" from another user's (e.g., User B) perspective.

This issue might arise as a result of a number of reasons, including as a result of the initialization process for MR headsets and devices. Often, for each MR peripheral or headset used in an MR system (e.g., each headset worn by individual users in a multiplayer game), the origin and orientation of the mapping coordinate system (i.e., coordinates of 0, 0, 0) is assumed to be the location and orientation of that device at the start of the mapping procedure. In practical terms, this is often the location and orientation of the device at the time of booting, turning on, starting a user session, waking, calibration or launching of an application requiring localization. For example, headset 120A might be used by User A and has an origin point located at A1. On the other hand, headset 120B might be used by User B and has an origin point located at B1. Origin location A1 and Environment A are significantly different compared to original location B1 and Environment B. For this reason, each device typically has an origin and mapping coordinate system that is different from each other device. In the illustrated example, the map of environment A that is used by User A is not coordinated with the map of environment B that is used by User B. If the coordinates associated with MR headsets 120 are not correctly translated between the headsets, their motion might be incorrectly represented. For example, forward movement by User B's avatar might incorrectly appear as the left-to-right movement or reverse movement in User A's headset.

This issue is addressed by the present system through a process known as spatial alignment whereby the position and orientation of each of the objects of interest (e.g., MR headsets, MR devices, etc.) are associated in a fixed relationship with an established point of reference that also has a fixed position and orientation in the real world. More particularly, as further discussed below, a plurality of anchors that each have a fixed position in space are used to define an alignment vector E having a specific position and orientation in space and that has a specific position and orientation with respect to each of the objects of interest. Thus, through these fixed relationships and the alignment vector E, the relative position and orientation of each of the objects of interest can be related to one another even across different coordinate systems.

Figure 10:
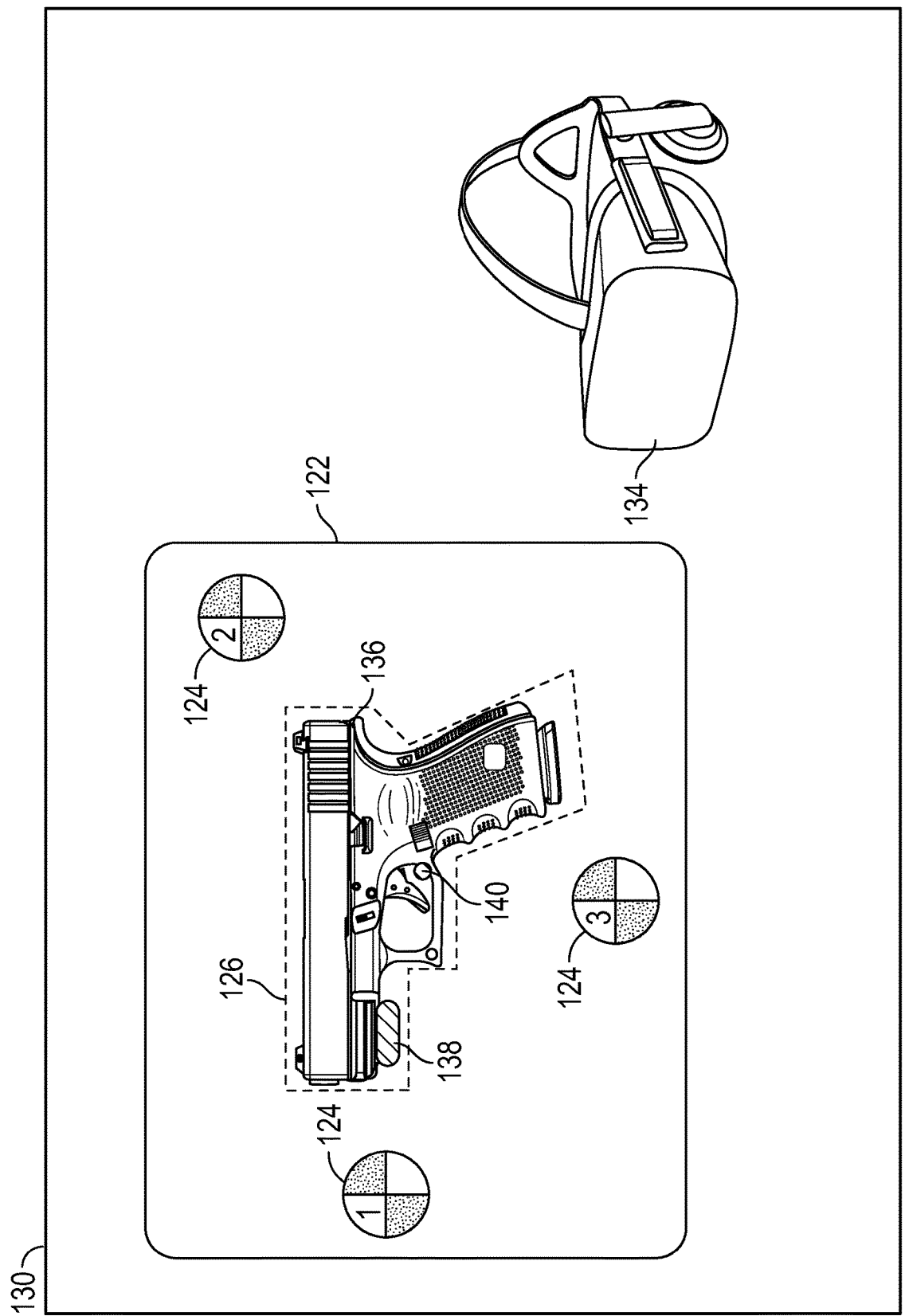
FIGS. 10 and 11 depict a template mat having a plurality of anchors that is used in an anchoring process according to an embodiment of the present invention.
Figure 11:
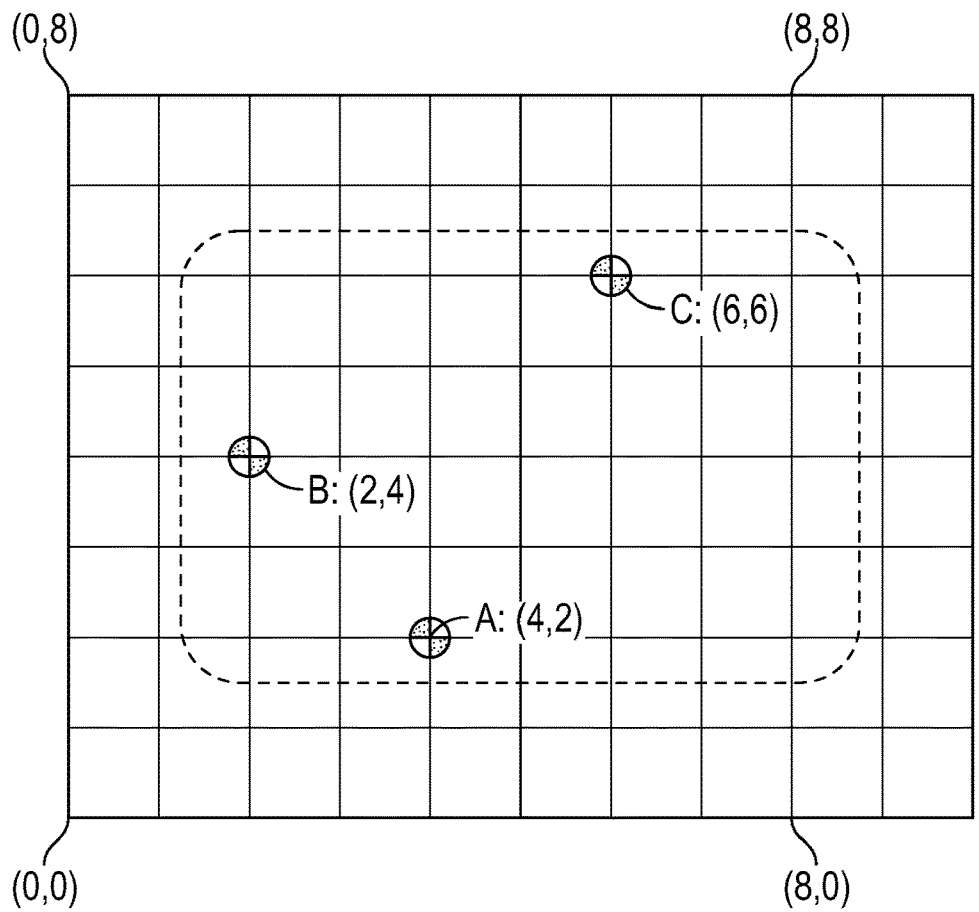
Figure 12:
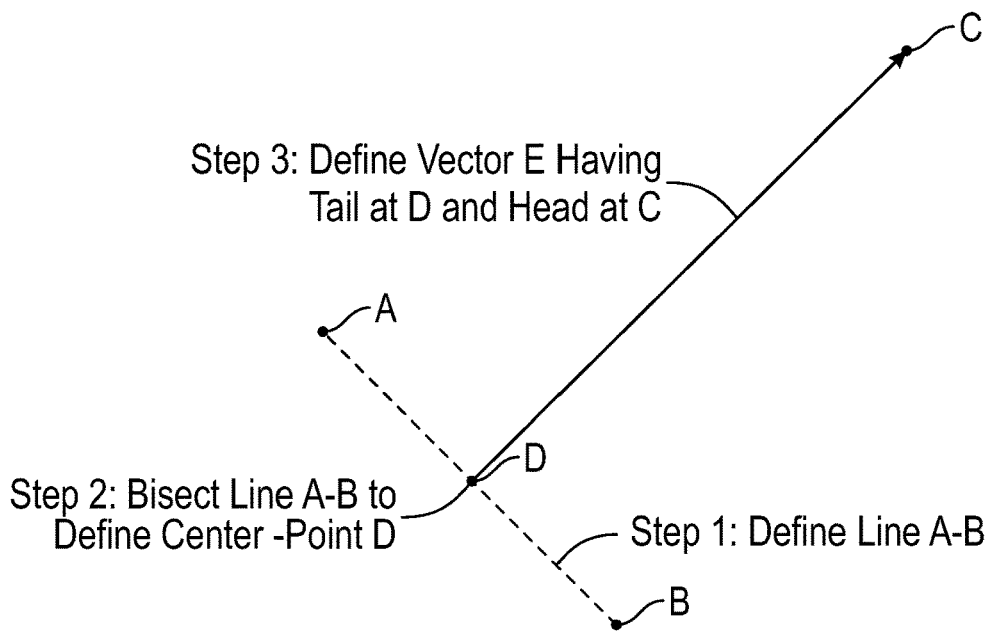
FIG. 12 shows the anchor points shown in FIGS. 10 and 11, represented as points A thru C, and also showing a mid-point D of bisected line A-B and also vector E extending from D to C.

With reference to FIGS. 10-12, the spatial alignment process is carried out by first establishing a plurality of anchors 124 (three anchors 124-1, 124-2, 124-3 are shown in FIG. 10), which are fixed in space and which are used in establishing an alignment vector E. While the absolute location of those tracked objects within a given coordinate system may differ, the anchor points 124 are defined as being located at the same physical location and rotation for each device/object, regardless of coordinate system. In this way, the physical world is used as the "Coordinate System of Record." Locations of the tracked objects are then synced by triangulating relative to the anchors, maintaining spatial alignment regardless of movement.

As shown in FIG. 12, the alignment vector E is established by first defining a line A-B that extends between points A and B, whose positions correspond to two of the locations of the anchors 124. Next, line A-B is bisected to define a center point D. Finally, the vector E is defined by a line having a tail at center point D and a head located at point C. Once the alignment vector E is established, the other objects of interest can use that vector to relate the position and orientation of their subjective coordinate system to the position and alignment of the vector. The value of using a vector is that it not only establishes a position but it also establishes a fixed orientation as well. The embodiment shown is a 2-dimensional example. However, the same process could be used in 3-dimensional cases as well. The anchoring process, itself, can be accomplished either through tagging (e.g., with the MR system's peripheral) or through the placement of defined images whose locations can be tagged by the MR system via image tracking. Tagging requires the user to mark a physical location using a MR peripheral that is tracked directly by the MR system. Once targets are located at each designated anchor location, a user might then place an MR peripheral at the anchor and press a button to record the location of that target within the MR system. Users of other MR systems, such as other players in a multiplayer game, can also tag the same targets, allowing the devices to have a common point of reference in the physical space.

Although not strictly necessary, in preferred embodiments, a minimum of 3 anchor points is used to enable triangulation of the initial starting position of the object being tracked. With a sufficiently precise tracking system, a single anchor point could be used to establish position and orientation, but a minimum of 3 anchor points is preferred. By triangulating the initial starting position of the object of interest with 3 anchor points, the position and orientation of the object being tracked (in some cases, the object's IMU) in 3D space can be tracked. Additionally, the use of 3 anchor points also lowers uncertainty due to sensor or user error. Of course, the use of more than 3 anchor points will further lower the uncertainty in determining the starting position and movement of the object.

In order to accurately define orientation, the anchoring process used should be consistent and reliable from one tracked object to the next in order to allow tracking across varying map coordinate systems (e.g., such as those generated by SLAM over different user sessions). In other words, the anchor locations in physical space relative to the object being tracked and the affixed location of the IMU(s) must be the same for every anchoring session. Since the starting location of the object being tracked (and the IMU associated with that object) is estimated based on the relative location of the anchors, if the relative locations change, the tracking will no longer have knowledge of the starting location of the IMU in physical space.

As such, in preferred embodiments, anchoring is done via a template, such as a template mat 122. In preferred embodiments, template mats 122 include a defined area 126 onto which objects of interest are placed and that establish a fixed position for those objects with respect to those anchor points (e.g., centered between all of the anchor points). A template mat 122 can be as simple as a piece of paper or another surface specifically designed for the object (e.g., a rubber or foam mat with cut-outs specific to the dimensions of the object to secure it in the defined location). Template mats 122 are not necessary and could be replaced by a plurality of points that are fixed in space, but they are helpful. Template mats 122, which can be generated for any object that is to be tracked, provide a way for the object to be consistently placed relative to the anchors 124 for initial alignment. Preferably, multiple anchor points 124 are defined on a single template mat 122.

Additionally, anchors should be tagged in a defined order (e.g., 124-1, 124-2, 124-3) or the image tagging use distinct images with defined placement. It is noted that the anchor locations 124 do not necessarily need to be located at the IMU locations, but they can be located at the IMU locations. In any case, the object to be tracked should remain stationary and in a fixed orientation relative to the anchors 124 during the tagging process to ensure the object's (and IMUs') relative position to the anchors is accurately reflected in the anchoring procedure.

Finally, with the object spatially aligned to the MR system's map coordinate system and a starting position defined, the object can be tracked in real-time using one of the tracking methods described above (e.g., via the IMU data that the MR system receives from the IMUs). Through the use of kinematics, the position and orientation of the object can be determined and tracked based on the object's acceleration along 6 dimensions (i.e., 3 translational dimensions, 3 rotational dimensions) over time. Tracking should begin immediately after the completion of the tagging process and prior to movement of the object from the anchored starting position. Otherwise, if the object is moved prior to initialization of tracking, the defined starting location is no longer reliable. In preferred embodiments, the MR system can be configured to automatically begin tracking at the completion of tagging. Advantageously, computational complexity of these determinations is minimal, allowing for robust tracking even on MR systems with limited computational power. The limitation of tracking speed becomes the Bluetooth latency.

EXAMPLES

Figure 14:
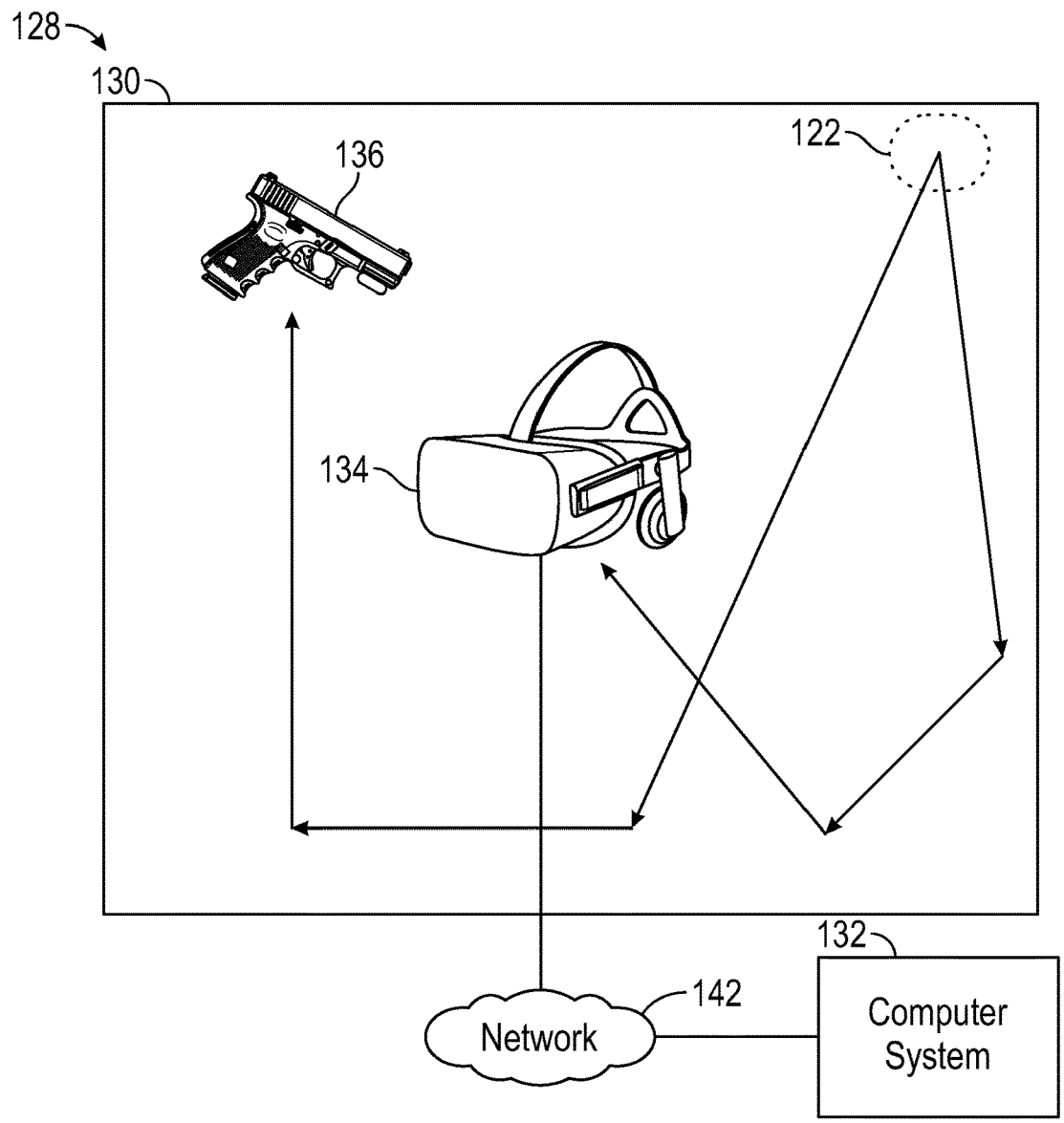
FIG. 14 depicts a portion of an MR training system according to an embodiment of the present invention.
Figure 15:
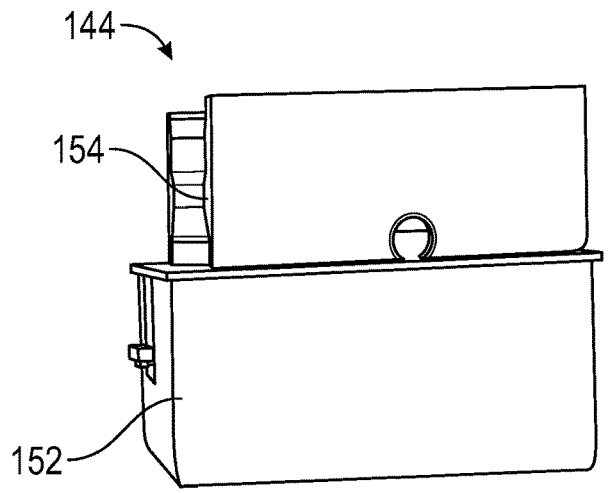
FIGS. 15-20 depict three prototype devices for mounting inertial measurement units (IMUs) to real world devices.

Now, with further reference to FIG. 14, this example makes use of the Skeletal System methodology (specifically a "root bone" implementation) to provide spatial positioning of an object.

Here, a training system 128 is used in a training environment 130 according to an embodiment of the present invention is depicted. In this particular case, the training system 128 provides a pistol training simulation that might be used, for example, by law enforcement or military personnel. The system 128 includes a mixed reality (MR) system that includes a computer system 132 for generating content and/or delivering that content to users of the system via a user display 134, which user display may be provided as goggles or a headset. The system 128 may include more than one computer system 132. For example, a separate computer system 132 may be provided for each user of the system 128. In another example, the computer system 132 includes a first computer (or server) for generating and delivering content to the user displays 134 using a second computer, such as a microcontroller or a microcomputer.

Preferably, the training system also includes at least one MR peripheral device 136 that is paired with the user display 134 and is used by the user for interacting with the training content. In this case, the MR peripheral device 136 includes a gas-actuated pistol (e.g., Airsoft gun) having one or more sensors for tracking the real-time position and motion of the device. In this case, an IMU 138 is mounted below the barrel of the pistol. IMU 138 may include a microcontroller, whose purpose is to collect data from itself as well as additional chipsets. More specifically, the IMU 138 is this particular embodiment is a 9 degree of freedom (9-DOF) absolute orientation IMU fusion chipset. It consists of an accelerometer, magnetometer, and gyroscope along with a central processing unit (CPU). The CPU ingests all the sensor data and generates the absolute orientation as Euler angles by transforming the data via a fusion algorithm. Several fusion algorithms exist, such as the Mahony and Madgwick algorithms. However, most commercially available chipsets ship with a proprietary algorithm that refines these known methods for the specific hardware. The Taidacent BNO08X chipset was used here and provided 3-dimensional orientation information in Euler angles (or, optionally, in quaternions) to the microcontroller. A custom sensor fusion was used to combine the microphone and orientation data and is independent of Mahony and Madgwick's algorithms. By combining the microphone data with the IMU data, this device is able to determine when the slide has been racked to load the firearm. Additionally, the device is able to determine between the following: acceleration from a single fire, a user running with the gun, another nearby user firing a different gun, and other false positives. The entire device is powered by high density, low cost LIPO battery packs. In this case, off-the-shelf USB-C based circuits were used to power the system and to provide 24 hours of power on a single charge.

In addition, the microcontroller used preferably contains custom code which performs filtering and transformation of the data, including adjudication of whether a shot has been fired or switch has been activated. Here, a switch 140 is mounted behind the trigger and is contacted when the trigger is pulled. Other sensors may be provided to provide other information related to the pistol or its function. For example, sensors may be provided to detect when the slide of the pistol is racked, to detect when the magazine is released and replaced, and to detect the ammo count.

The high sampling rate of the hardware vs. the acceptable response rate of the system allows for the data to be filtered using a low-pass filter. This ensures that the acceleration profile seen is due to the gun firing and not related to other noise sources such as a user running or racking the slide to load a new magazine. In some cases, high sampling rates resulted in the impression that the user was firing a machine gun in some cases when they were not. This problem was solved by utilizing sensor fusion with the microphone, which permits the firing events to be narrowed to a singular physical event. As a result, given this approach the user could drop the gun, which would result in a massive impulse, without register an event. Additionally, if another user fires a gun nearby, an event was also not be triggered.

Preferably, sensor fusion occurs on the microcontroller and a subset of the data is transmitted over Bluetooth to the MR peripheral (computer system 132). In this particular embodiment, the IMU/microcontroller 318 makes use of Bluetooth Low Energy (BLE) notifications. The microcontroller 138 acts as a GATT server which provides a GATT notification to which the MR peripheral can subscribe to receive real-time updates of the data as the microcontroller makes them available. In preferred embodiments, at least a portion of the communication between the user display 134 and the computer system 132 is over a wireless network 142. For example, real-time updates of data could be provided over wireless, WiFi or wired connections. Preferably, the data is encoded in such a way as to minimize the amount of data transferred. This speeds up the data transfer, allowing use to still render things at 30 frames per second or faster. This particular prototype uses the Arduino Nano 33 BLE Sense microcontroller, and delivers the following output data derived (using custom code running on the microcontroller) from the raw data feeds it collects: Shot fired/Switch activated, 3D rotation, and Timestamp.

When the system 128 is in use, a first step is to place the template mat 122 into a fixed location. Next, each MR peripheral device 136 is placed onto the mat 122 and tagged, which aligns each of their coordinate systems. Then, as indicated by the arrows, the computer system 132 is able to the movement of the headsets 134 and MR peripherals 136 within the training environment 130. During that training experience, the user might encounter armed assailants and must then decide when to use deadly force. By using the gas-actuated pistol 136 with haptic feedback, the user experiences the actual weight and feel of the equipment. In the case of activities such as police training this can crucially allow the user to train on replicas of the very same pistols they will use in real events. The IMU 138 allows the pistol 136 position to be tracked either by the headset 134 and/or by the computer system 132. This, in turn, enables the application to know where the pistol 136 is positioned and pointing. Activating the switch 140 allows the user to fire the pistol 136 in the virtual environment 130 while simultaneously feeling the recoil from the gas blowback. Because of the integrated tracking, performance data such as firearm accuracy and number of shots fired can also be tracked and measured.

Figure 13:
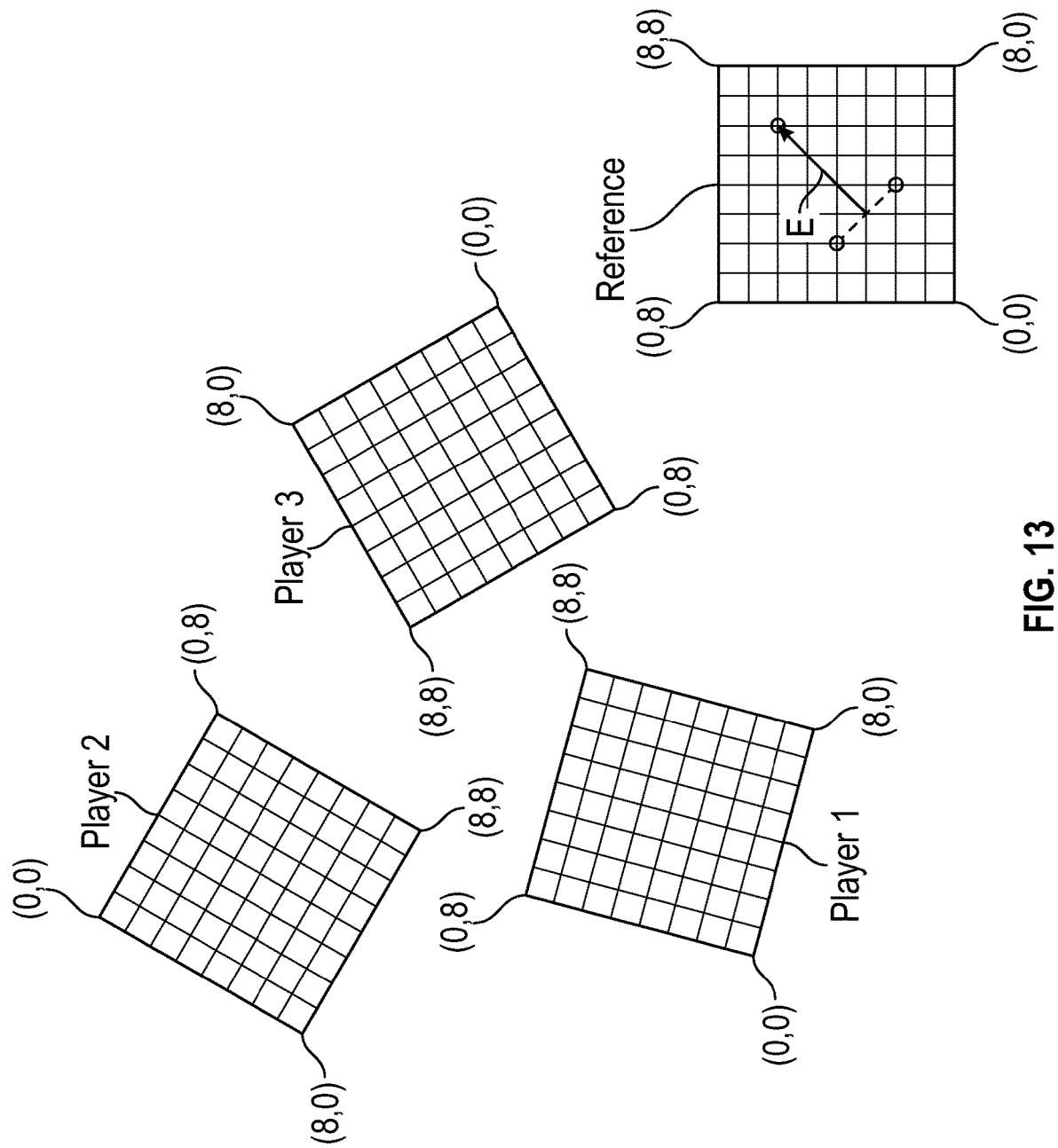
FIG. 13 depicts mapped environments for Player 1 thru Player 3 and also showing a Reference environment that includes vector E of FIG. 12, which vector is used in a spatial alignment process according to an embodiment of the present invention.
Figure 16:
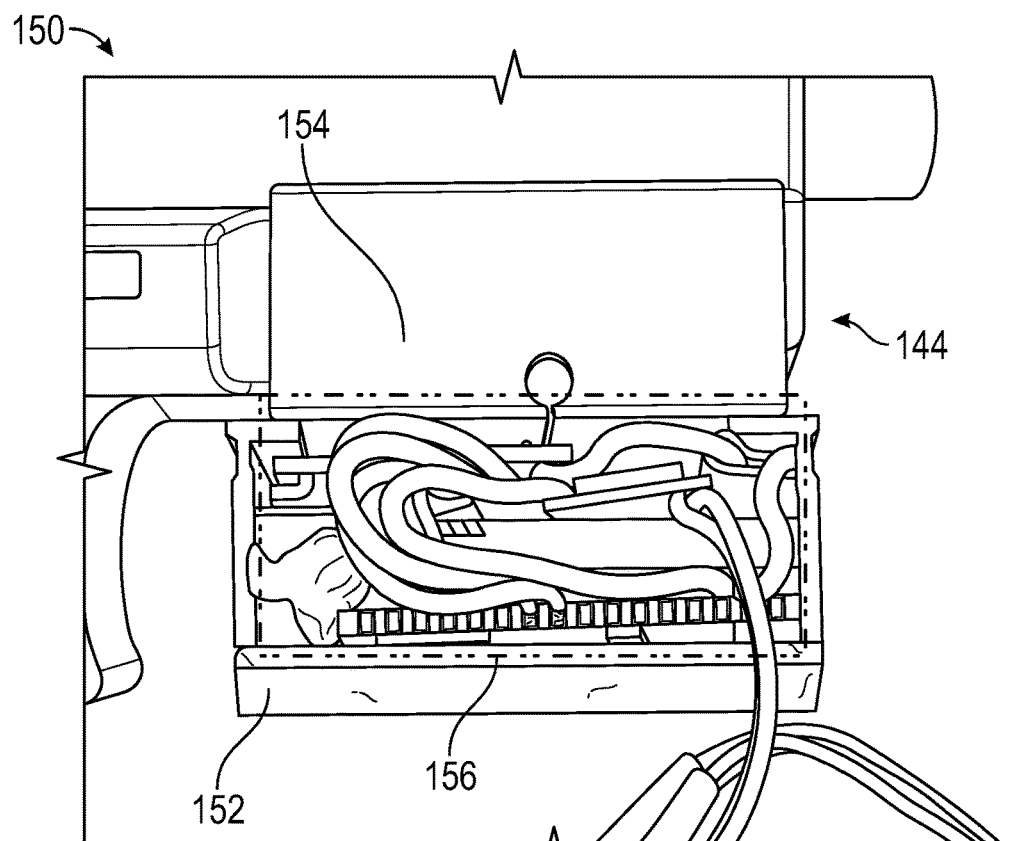

With reference to FIGS. 15-20, three prototypes 144, 146, 148 are shown for mounting IMUS to real world devices (airsoft guns 150, in each of the illustrated cases). In each case, the housings 152 provided by such prototypes 144, 146, 148 include an appropriate mounting interface for securely but removably attaching to those devices (i.e., to the airsoft guns 150). For example, in FIG. 13-15, a first mount 144 for an airsoft pistol 150 is shown. In this case, the various components 156 are fitted into a housing 152. In this case, the housing includes an attachment point 154 that can be attached or integrated directly with an attachment for a MIL-STD-1913 standard rail interface system, also known as a Picatinny rail mount. The hardware provides 3D orientation of the device over BLE, which is further constrained via the Root Bone methodology discussed previously to determine the 3D position and orientation of the device. Other IMUs may be configured to interface with firearm holsters, which would be beneficial in training correct holstering of the weapon. FIG. 16 shows an alternative mounting device that includes a housing 152 that stores various components 156 that provide 3D tracking via IMUs' constrained visual odometry.

Figure 17:
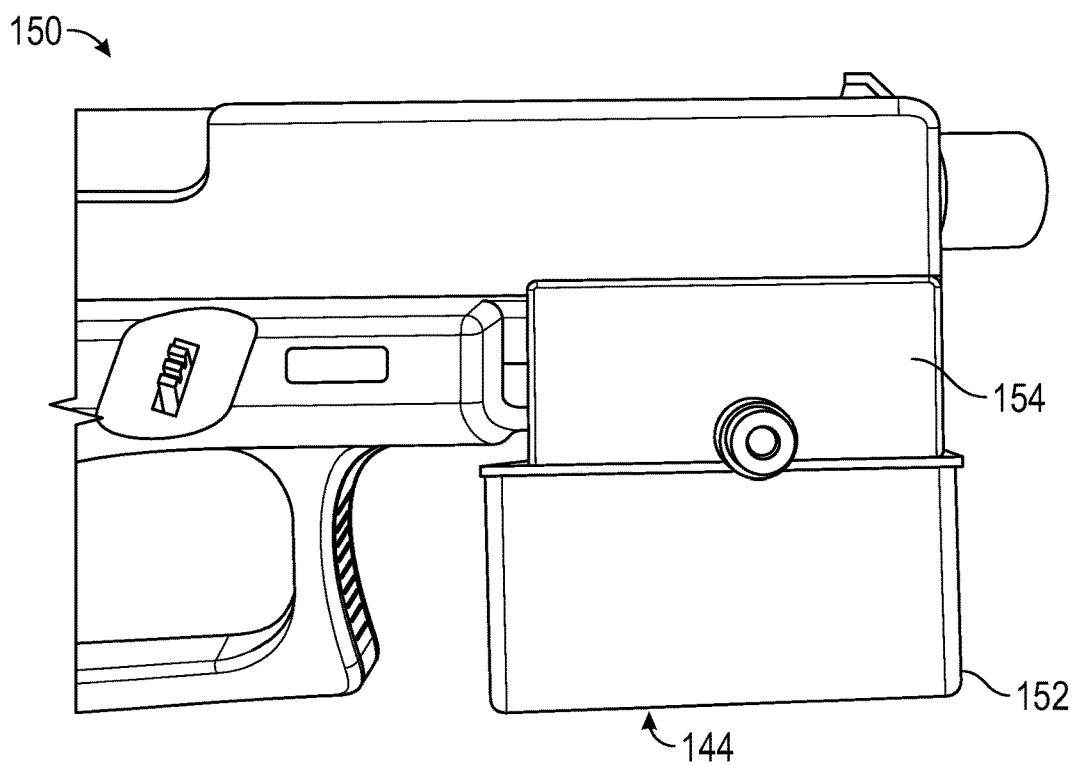
Figure 18:
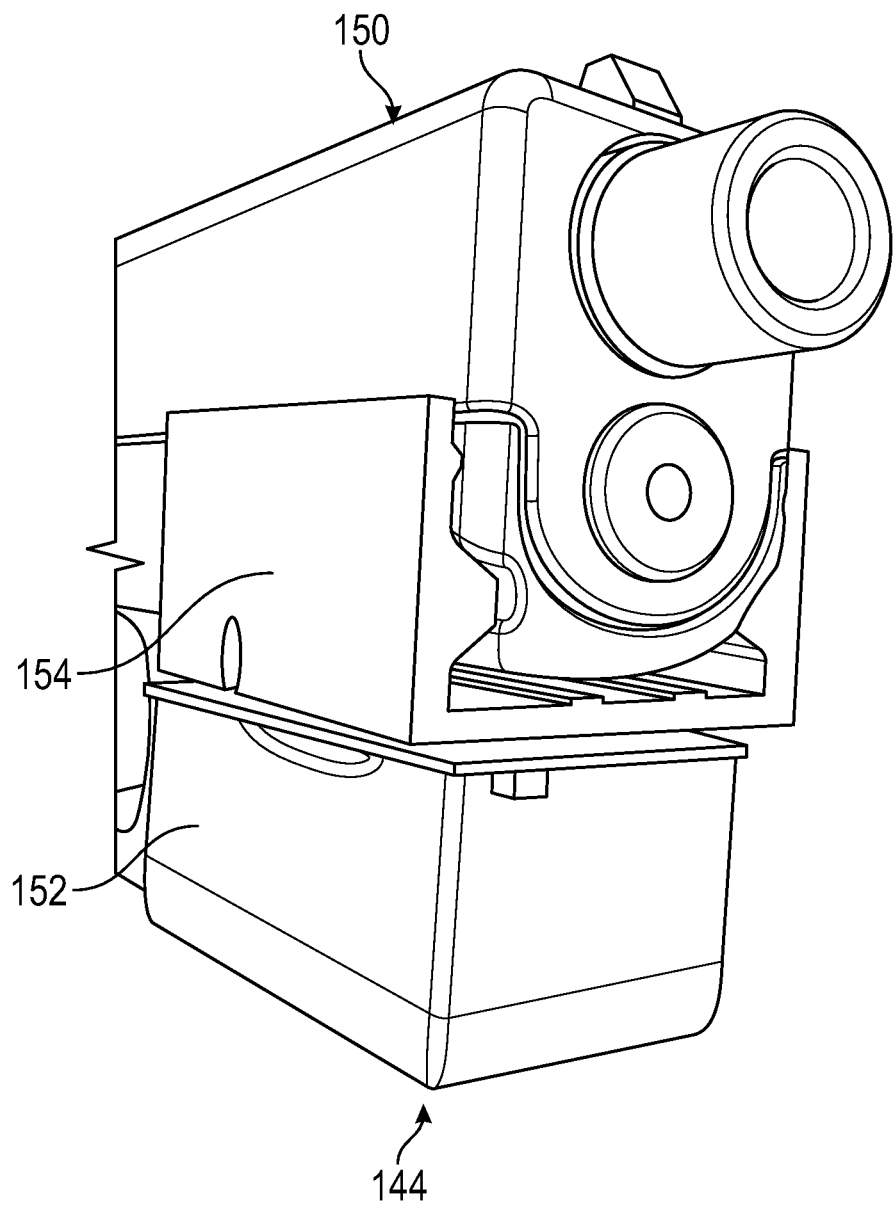
Figure 19:
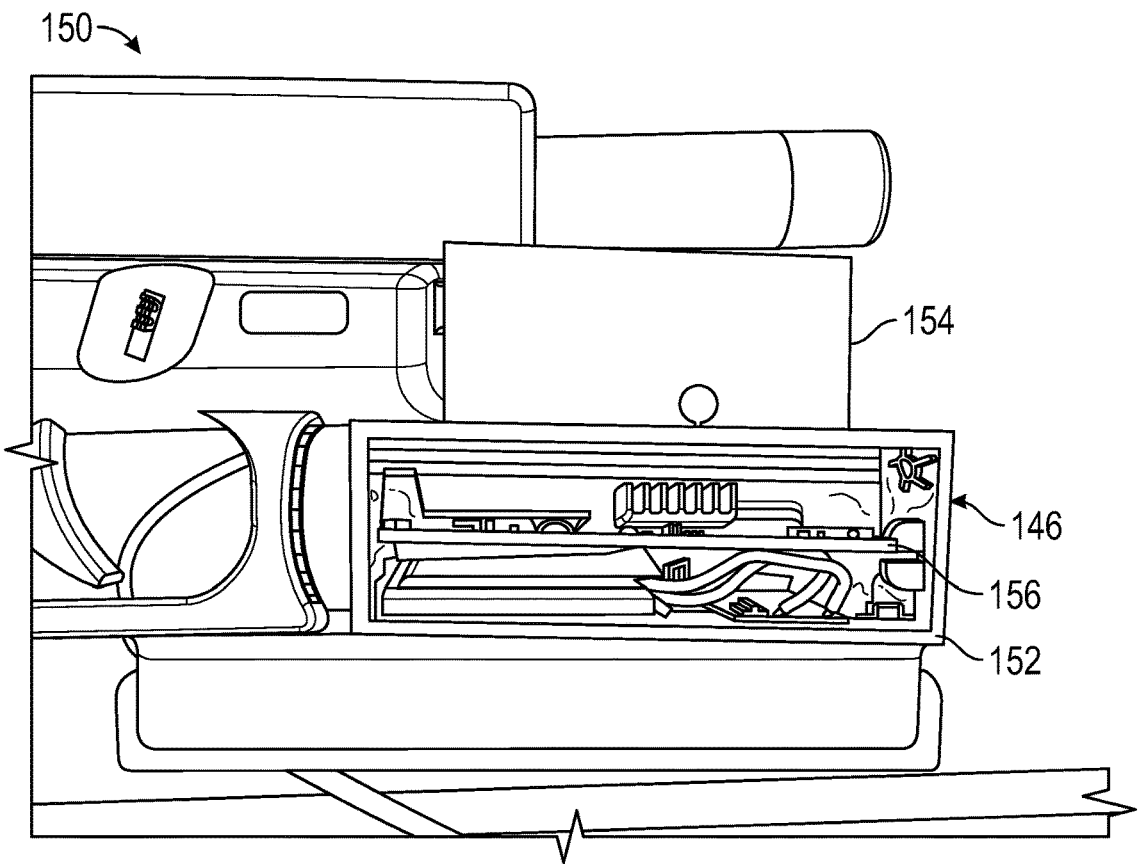
Figure 20:
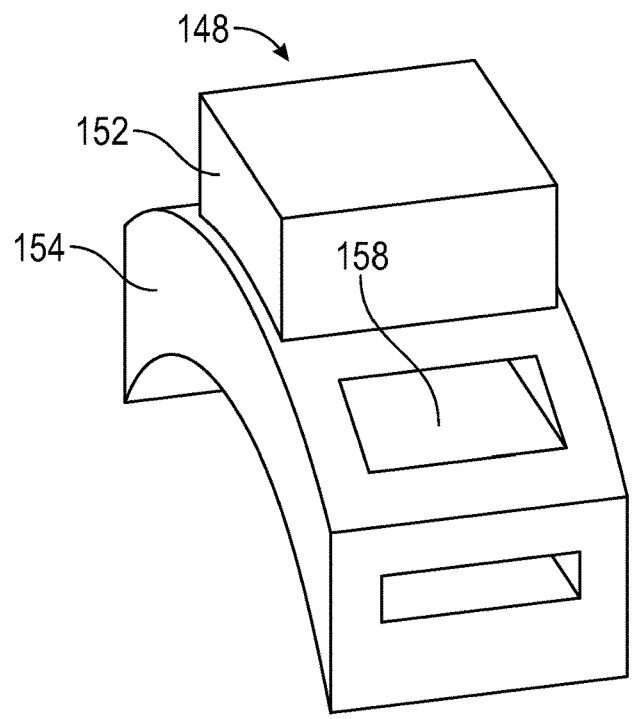

While the example given above related to a pistol, other similar devices may be used for providing similar training scenarios, including in other fields. For example, a rifle or fire hose nozzle may be similarly equipped with IMUs and switches as well as other sensors (e.g., switch magnet, reed switch, etc.). Similarly, as shown in FIG. 17, an apparatus 148 for use in tracking a fire hose nozzle may include a mounting interface that includes a cylindrical mold 154 that is sized to match the outer circumference of the fire hose nozzle. The mold 154 may include cutouts 158 on either side (one is shown) that are sized and configured to receive mounting straps for removably mounting the hose. Mounting may also be accomplished through the use of high-powered magnets in place of or alongside of the straps. The mounting system also includes a hardware housing 152 for safely storing the same types of sensors described above for the pistol that are used for tracking the use of the fire hose. In many cases, fire departments use a standard size nozzle such as a 1¾ inch from common brands such as Task Force Tips, allowing for a standardized mountings across multiple fire hoses.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations as would be appreciated by those having ordinary skill in the art to which the invention relates.

What is claimed is:

1. A mixed reality (MR) training system comprising:
a computer system; and
a display configured to display an MR environment,
wherein the computer system comprises:
a scenario identification algorithm (ML1) configured to take, as inputs from a first data source, data related to one or more incidents of concern (IOC) within a data set of one or more incidents, wherein the data set includes incident report data related to the one or more incidents and contextual data that relate to the one or more incidents, and wherein each IOC is an incident that appears in the data set from the first data source with a frequency at least equal to a tunable frequency threshold or wherein contextual data related to the IOC indicates a resulting consequence that is at least equal to a pre- determined resulting consequence threshold, to identify incidents that are IOCs based on the frequency of the incidents in the first data source or the resulting consequence of the incident; and
a machine learning-aided content generation algorithm (ML3) configured to receive the IOC identified by the ML1, and to generate a training simulation comprising computer-generated MR training content incorporating at least one of a pre-generated MR training content building block from a pre-existing library of content, the MR training content building blocks comprising at least one of human entities building block, environment building block, and experiential building block, based on at least one of the identified IOCs; and wherein the computing system is configured to output said computer-generated training simulation comprising the generated MR training content to a user of the system via the display.

2. The system of claim 1 wherein at least one of the IOCs identified is identified as an IOC as a result of the incident being a type of incident wherein performance data that is related to a user's performance on the MR training content involving that same type of incident indicates that the user's performance needs improvement.

3. The system of claim 1 wherein at least one of the IOCs identified is identified as an IOC as a result of the incident being a type of incident wherein performance data that is related to a user's performance on the MR training content involving that same type of incident indicates that the user's performance needs improvement.

4. The system of claim 1 further comprising a scenario prediction algorithm (ML2) configured: to also take, as inputs from the first data source, the incident report data and contextual data; and from those inputs, to output to the ML3 predicted data that includes either (i) predicted changes in a frequency of an identified type of incident occurring in the incident report data or (ii) predicted changes in contextual data of the incidents occurring in the incident report data, wherein the ML3 is further also configured to generate MR training content based, at least in part, on the predicted data provided by the ML2.

5. The system of claim 3, wherein the ML2 identifies possible incidents using mathematics and based on either an extrapolation or combination of incidents within the incident report data.

6. The system of claim 3 wherein the predicted changes in contextual data of incidents occurring in the incident report data include changes to resulting consequences from the one or more incidents.

7. The system of claim 3 wherein the ML2 is further configured:
to identify at least one of (i) a likelihood of that incident occurring again or (ii) how novel the incident is compared to other incidents in the incident report data; and
to identify at least one enhancing factor within the contextual data that is common between two or more similar incidents identified by the ML2 that impact the likelihood of that incident occurring again or that impacts how novel the incident of the IOC is compared to other incidents included in the incident report data.

8. The system of claim 7 wherein the ML2 is further configured to identify likelihood of failure.

9. The system of claim 6 wherein the ML3 is further configured to generate the MR training content by prioritizing at least one of the likelihood of that incident occurring again or how novel the incident is compared to other incidents in the incident report data.

10. The system of claim 6 wherein the ML3 is further configured to generate the MR training experiences based on the enhancing factor and utilizing an objective function that maximizes the likelihood of occurrence and novelty of the incident upon which the MR training experience generated is based.

11. The system of claim 1 wherein the ML3 is configured to generate MR training content portions on-the-fly based on recommendations based on performance data, user biometric response data, and user demographic data.

12. The system of claim 1 wherein the ML3 is further configured to automatically combine two or more of the pre-generated MR training content building blocks in order to generate a new MR training content.

13. The system of claim 1 wherein the MR training content generated by the ML3 includes one or more content injection points, wherein MR content occurring before each content injection point is configured to enable a plurality of MR training content portions to be seamlessly substituted such that the MR training content may be customized to provide two or more different MR training contents experience by substituting a first training content portion for a second training content portion at the one or more content injection points.

14. The system of claim 13 wherein placement of the one or more content injection points within the MR training content is event driven and is based on an occurrence of a predetermined action carried out by a user or a predetermined event occurring within the MR training content.

\* \* \* \* \*